United States Patent [19]

Cozzi et al.

[11] Patent Number: 5,280,033
[45] Date of Patent: Jan. 18, 1994

[54] SUBSTITUTED 1-(ALKOXY-IMINOALKYL) IMIDAZOLE DERIVATIVES AND THEIR USE IN TREATING DISEASE RELATED TO AN ENHANCEMENT OF THROMBOXANE-$A_2$ SYNTHEIS

[75] Inventors: Paolo Cozzi; Marla Menichincheri, both of Milan; Arsenia Rossi, Dalmine; Corrado Ferti, Barlassina; Patricia Salvati, Arese, all of Italy

[73] Assignee: Farmitalia Carlo Erba S RL, Milan, Italy

[21] Appl. No.: 768,568

[22] PCT Filed: Feb. 26, 1991

[86] PCT No.: PCT/EP91/00351
§ 371 Date: Oct. 25, 1991
§ 102(e) Date: Oct. 25, 1991

[87] PCT Pub. No.: WO91/13062
PCT Pub. Date: Sep. 5, 1991

[30] Foreign Application Priority Data

Feb. 27, 1990 [GB] United Kingdom ............... 9004347
Dec. 19, 1990 [GB] United Kingdom ............... 9027551

[51] Int. Cl.⁵ .................. A61K 31/44; A61K 31/415; C07D 409/06; C07D 233/61
[52] U.S. Cl. .................. 514/341; 514/63; 514/397; 514/399; 546/278; 548/110; 548/315.1; 548/336.1
[58] Field of Search ............. 548/110, 341, 315.1, 548/, 336.1; 514/63, 399, 341; 546/278

[56] References Cited

U.S. PATENT DOCUMENTS 4,352,804  10/1982  van Zorge ............... 548/336.1
4,599,348  7/1986  Schmetzer et al. ........ 548/336.1
4,797,412  1/1989  Knobs et al. ............. 548/336.1

FOREIGN PATENT DOCUMENTS 0028346  5/1981  European Pat. Off. .
0065107  11/1982  European Pat. Off. .
0158299  4/1984  European Pat. Off. .
0132771  2/1985  European Pat. Off. .
0142653  5/1985  European Pat. Off. .
3545085  12/1985  Fed. Rep. of Germany .

Primary Examiner—Patricia L. Morris
Attorney, Agent, or Firm—Nikaido, Marmelstein, Murray & Oram

[57] ABSTRACT

1-(Alkoxy-iminoalkyl)imidazole derivatives of formula

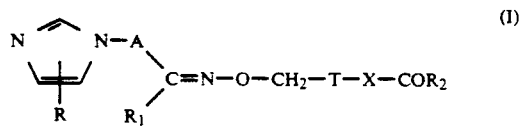

(I)

wherein R is hydrogen or $C_1$-$C_4$ alkyl; A is $C_1$-$C_4$ alkylene optionally substituted by phenyl optionally substituted by halogen or trifluoromethyl; R is (a) hydrogen or a $C_1$-$C_{10}$ hydrocarbon radical; (b) an aryl or aryl-$C_1$-$C_4$ alkyl group wherein the said aryl is optionally substituted either by halogen, trihalo-methyl, $C_1$-$C_4$ alkyl, $C_2$-$C_3$ alkenyl, $C_2$-$C_6$ alkynyl, $C_1$-$C_4$ alkoxy, $C_1$-$C_4$ alkylthio or $C_1$-$C_4$ alkylsulfonyl or by $C_5$-$C_8$ alkyl, $C_4$-$C_8$ alkenyl, $C_5$-$C_8$ alkoxy, $C_5$-$C_8$ alkylthio or phenyl optionally substituted by halogen, trihalomethyl or $C_1$-$C_4$ alkyl; or (c) a $C_5$-$C_8$ cycloalkyl or $C_5$-$C_8$ cycloalkyl-$C_1$-$C_4$ alkyl group, wherein the said cycloalkyl is optionally substituted by $C_1$-$C_4$ alkyl; T is a $C_1$-$C_6$ hydrocarbon chain or phenylene; X is a bond, —O—$CH_2$—, —C(R' R")—, Si(R' R")—, vinylene or isopropenylene, each R' and R" being hydrogen, fluorine or $C_1$-$C_4$ alkyl; and $R_2$ is —$OR_3$ or —N($R_3R_4$), each $R_3$ and $R_4$ being hydrogen, $C_1$-$C_6$ alkyl, phenyl or benzyl; and the pharmaceutically acceptable salts thereof; are useful in the treatment of a disease state related to enhancement of thromboxane $A_2$ (Tx$A_2$) synthesis.

9 Claims, No Drawings

SUBSTITUTED 1-(ALKOXY-IMINOALKYL) IMIDAZOLE DERIVATIVES AND THEIR USE IN TREATING DISEASE RELATED TO AN ENHANCEMENT OF THROMBOXANE-$A_2$ SYNTHEIS

This application is a continuation (i.e., the U.S. national phase) of PCT International Application No. PCT/EP91/00351, filed Feb. 26, 1991.

The present invention relates to new 1-(alkoxyiminoalkyl) imidazole derivatives, to a process for their preparation, to pharmaceutical compositions containing them and to their use as therapeutic agents.

The present invention provides novel compounds having the general formula (I)

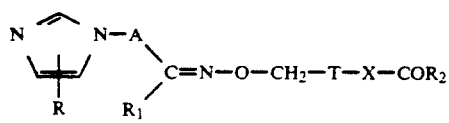

wherein

R is hydrogen or $C_1$-$C_4$ alkyl;

A is a $C_1$-$C_4$ alkylene chain unsubstituted or substituted by a phenyl ring unsubstituted or substituted by one or two substituents chosen independently from halogen and trifluoromethyl;

$R_1$ is a) hydrogen or a straight or branched, saturated or unsaturated $C_1$-$C_{10}$ hydrocarbon radical; b) an aryl or aryl-$C_1$-$C_4$ alkyl group, wherein the aryl group or the aryl moiety is unsubstituted or substituted either by one to four substitutents independently chosen from halogen, trihalomethyl, $C_1$-$C_4$ alkyl, $C_2$-$C_3$ alkenyl, $C_2$-$C_6$ alkynyl, $C_1$-$C_4$ alkoxy, $C_1$-$C_4$ alkylthio and $C_1$-$C_4$ alkylsulfonyl or by a substituent chosen from $C_5$-$C_8$ alkyl, $C_4$-$C_8$ alkenyl, $C_5$-$C_8$ alkoxy, $C_5$-$C_8$ alkylthio and phenyl, in which the phenyl ring is unsubstituted or substituted by a substituent chosen from halogen, trihalomethyl and $C_1$-$C_4$ alkyl; or (c) a $C_5$-$C_8$ cycloalkyl or $C_5$-$C_8$ cycloalkyl-$C_1$-$C_4$ alkyl group, wherein the cycloalkyl group or moiety is unsubstituted or substituted by one to three $C_1$-$C_4$ alkyl groups;

T is a straight or branched, saturated or unsaturated $C_1$-$C_6$ hydrocarbon chain, or a phenylene radical;

X is a bond or a divalent group consisting of $-O-CH_2-$, $-C(R'R'')-$, $-Si(R'R'')-$, vinylene or isopropenylene, wherein each of $R'$ and $R''$ being the same or different is hydrogen, fluorine or $C_1$-$C_4$ alkyl;

$R_2$ is an $-OR_3$ or $-N(R_3R_4)$ group, wherein each of $R_3$ and $R_4$ independently is hydrogen, $C_1$-$C_6$ alkyl, phenyl or benzyl; and the pharmaceutically acceptable salts thereof.

The invention also includes within its scope all the possible isomers, stereoisomers and their mixtures and the metabolites and the metabolic precursors or bioprecursors of the compounds of formula (I).

In particular the compounds of formula (I) exhibit either E or Z isomerism about the oximic double bond. Both the single E and Z isomers of the compounds of formula (I) and their mixtures are also included within the scope of the present invention.

The alkylene chain A may be, independently, a straight or branched chain, unsubstituted or substituted, as defined above. Typically $-CH_2-$, $-CH_2-CH_2-$, $-CH_2-CH_2-CH_2$,

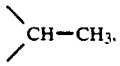

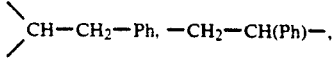

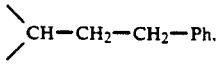

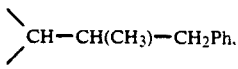

$CH_2-CH(CH_2Ph)-$ and $-CH-CH_2-CH(CH_3)-Ph$, wherein Ph represents a phenyl ring as defined above.

When $R_1$ is a $C_1$-$C_{10}$ hydrocarbon radical as defined above under a), it is preferably a $C_1$-$C_8$ alkyl or $C_2$-$C_9$ alkenyl radical, for example $C_2$-$C_8$ alkenyl, in particular pentyl, hexyl and heptyl or propenyl and butenyl, respectively.

When $R_3$ and/or $R_4$ is a $C_1$-$C_6$ alkyl group it is, e.g., methyl, ethyl, propyl, isopropyl, butyl or tert.butyl, more preferably methyl or ethyl.

When $R_1$ is an aryl or arylalkyl group as defined above under b), the aryl group or the aryl moiety may be an aromatic or heteroaromatic group, for example phenyl, pyridyl, thienyl and naphthyl, in particular phenyl, pyridyl and thienyl. According to the definition of $R_1$ as an aryl or arylalkyl group given hereabove, a pyridyl group is preferably a 2- or 3-pyridyl group; a thienyl group is preferably a 2-thienyl group and a naphthyl group is preferably a 1- or 2-naphthyl group.

Accordingly, an arylalkyl group, as defined above, is preferably a phenyl-, thienyl- or pyridyl-$C_1$-$C_2$ alkyl group, in particular a benzyl, thienylmethyl or pyridylmethyl group. When $R_1$ is a cycloalkyl or cycloalkylalkyl group as defined above under c), the cycloalkyl group or the cycloalkyl moiety is preferably a cyclohexyl or cycloheptyl group. Accordingly, a cycloalkylalkyl group, as defined above, is preferably a cyclohexyl- or cycloheptyl-$C_1$-$C_2$ alkyl group, in particular cyclohexylmethyl or cycloheptylmethyl.

When T is a hydrocarbon chain it is preferably an alkylene or alkenylene, radical, for example a $C_1$-$C_5$ alkylene chain, in particular $-CH_2-$, $-CH_2-CH_2-$ or $-CH_2-CH_2-CH_2-$, $-CH_2-CH_2-CH_2-CH_2-$ or a $C_2$-$C_5$ alkenylene chain, in particular $-CH=CH-$, $-CH_2-CH=CH-$ or $-CH=CH-CH_2-$.

When T is a phenylene radical, it is e.g. a 1,2-, 1,3- or 1,4-phenylene, in particular a 1,3-phenylene radical. The alkyl, alkoxy, alkylsulfonyl and alkylthio groups may be branched or straight chain groups.

A $C_1$-$C_4$ alkyl group is e.g. methyl, ethyl, propyl, isopropyl, butyl or tert.butyl, more preferably methyl or butyl.

A $C_1$-$C_4$ alkoxy group is e.g. methoxy, ethoxy, propoxy, isopropoxy, butoxy or tert.butoxy, preferably methoxy, ethoxy or propoxy.

A $C_1$-$C_4$ alkylthio group is e.g. methylthio, ethylthio, propylthio or butylthio, in particular methylthio or ethylthio.

A $C_5$-$C_8$ alkyl group is preferably hexyl or heptyl.

A $C_2$-$C_3$ alkenyl group is preferably ethenyl.

A $C_4$-$C_8$ alkenyl group is preferably butenyl or hexenyl.

A $C_2$-$C_6$ alkynyl group is preferably a $C_2$-$C_4$ alkynyl group in particular ethynyl.

A $C_5$-$C_8$ alkoxy group is preferably pentyloxy or hexyloxy.

A $C_5$-$C_8$ alkylthio group is preferably pentylthio or hexylthio.

A halogen atom is suitably bromine, chlorine or fluorine, preferably it is bromine or fluorine.

A $C_1$-$C_4$ alkylsulfonyl group is preferably a methyl- or ethylsulfonyl, in particular methylsulfonyl, group.

A trihalomethyl group is e.g. trichloromethyl or trifluoromethyl, in particular trifluoromethyl.

Pharmaceutically acceptable salts of the compounds of the invention include acid addition salts, with inorganic, e.g. nitric, hydrochloric, hydrobromic, sulphuric, perchloric and phosphoric acids, an organic, e.g. acetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium, bases or alkaline-earth metal, especially calcium or magnesium, bases, or with organic bases, e.g. alkylamines, preferably triethylamine.

As stated above the present invention also includes within its scope pharmaceutically acceptable bioprecursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of the invention are the compounds of formula (I), wherein,

R is hydrogen or methyl;

A is a $C_1$-$C_4$ alkylene chain optionally substituted by phenyl, in its turn optionally substituted by one or two substituents independently chosen from halogen and trifluoromethyl;

$R_1$ is a) $C_1$-$C_8$ alkyl or $C_2$-$C_8$ alkenyl; b) a phenyl, naphthyl, thienyl or pyridyl group unsubstituted or substituted either by one or two substituents independently chosen from halogen, trihalomethyl, $C_1$-$C_4$ alkyl, $C_1$-$C_4$ alkoxy, $C_1$-$C_4$ alkylsulfonyl and $C_1$-$C_4$ alkylthio, or by a substituent chosen from $C_5$-$C_8$ alkyl, $C_4$-$C_8$ alkenyl, $C_5$-$C_8$ alkoxy, $C_5$-$C_8$ alkylthio and phenyl, in which the phenyl ring is unsubstituted or substituted by a substituent chosen from halogen, trihalomethyl and $C_1$-$C_4$ alkyl; or (c) a cyclohexyl or cycloheptyl group unsubstituted or substituted by one or two $C_1$-$C_4$ alkyl groups; T is a $C_1$-$C_5$ alkylene or $C_2$-$C_5$ alkenylene group; or a phenylene group;

X is a bond or a —O—$CH_2$— group;

$R_2$ is an —$OR_3$ or —$NHR_3$ group, wherein $R_3$ is hydrogen or $C_1$-$C_4$ alkyl; and the pharmaceutically acceptable salts thereof.

More preferred compounds of the invention are the compounds of formula (I), wherein, R is hydrogen;

A is —$CH_2$—, —$CH(CH_3)$—, —$CH_2$—$CH_2$— or —$CH(CH_2Ph)$— in which Ph means phenyl optionally substituted by a halogen atom;

$R_1$ is a) $C_5$-$C_7$ alkyl; b) a phenyl, pyridyl or thienyl ring, unsubstituted or substituted by halogen, $C_1$-$C_4$ alkyl, $C_1$-$C_4$ alkoxy or trifluoromethyl; or c) a cyclohexyl or cycloheptyl ring;

T is a $C_2$-$C_4$ alkylene or phenylene group;

X is a bond or a —O—$CH_2$— group;

$R_2$ is an —$OR_3$ group wherein $R_3$ is hydrogen or $C_1$-$C_4$ alkyl; and the pharmaceutically acceptable salts thereof.

Examples of specific compounds according to the present invention are the following compounds, either as Z or E-isomers or Z, E-mixtures of said isomers;

1) 5-[1-phenyl-2-(imidazol-1-yl)ethylidene]aminoxypentanoic acid;
2) 5-[1-phenyl-2-(imidazol-1-yl)ethylidene]aminoxypentanamide;
3) ethyl 4-[1-phenyl-2-(imidazol-1-yl)ethylidene]aminoxybutanoate;
4) 4-[1-phenyl-2-(imidazol-1-yl)ethylidene]aminoxybutanoic acid;
5) methyl 3-[1-phenyl-2-(imidazol-1-yl)ethylidene]aminoxypropanoate;
6) ethyl 5-[1-(3-trifluoromethylphenyl)-2-(imidazol-1-yl)ethylidene]aminoxypentanoate;
7) 5-[1-(3-trifluoromethylphenyl)-2-(imidazol-1-yl)ethylidene]aminoxypentanoic acid;
8) 5-[1-(3-bromophenyl)-2-(imidazol-1-yl)ethylidene]aminoxypentanoic acid;
9) 4-[1-(3-trifluoromethylphenyl)-2-(imidazol-1-yl)ethylidene]aminoxybutanoic acid;
10) 5-[1-(3-(n-butyl)phenyl)-2-(imidazol-1-yl)ethylidene]aminoxypentanoic acid;
11) 5-[1-(2-methoxyphenyl)-2-(imidazol-1-yl)ethylidene]aminoxypentanoic acid;
12) ethyl 3-oxa-5-[1-phenyl-2-(imidazol-1-yl)ethylidene]aminoxypentanoate;
13) 3-oxa-5-[1-phenyl-2-(imidazol-1-yl)ethylidene]aminoxypentanoic acid;
14) 3-oxa-5-[1-(3-trifluoromethylphenyl)-2-(imidazol-1-yl)ethylidene]aminoxypentanoic acid;
15) tert-butyl 5-[1-phenyl-2-(imidazol-1-yl)-2-methyethylidene]aminoxypentanoate;
16) 5-[1-phenyl-2-(imidazol-1-yl)-2-methyethylidene]aminoxypentanoic acid;
17) 3-[1-phenyl-2-(imidazol-1-yl)ethylidene]aminoxymethylbenzoic acid;
18) 4-[1-phenyl-3-(imidazol-1-yl)propylidene]aminoxybutanoic acid;
19) 5-[1-(n-hexyl)-2-(imidazol-1-yl)ethylidene]aminoxypentanoic acid;
20) ethyl 5-[1-cyclohexyl-2-(imidazol-1-yl)ethylidene]aminoxypentanoate;
21) tert-butyl 5-[1-cyclohexyl-2-(imidazol-1-yl)ethylidene]aminoxypentanoate;
22) 5-[1-cyclohexyl-2-(imidazol-1-yl)ethylidene]aminoxypentanoic acid;
23) ethyl 4-[1-cyclohexyl-2-(imidazol-1-yl)ethylidene]aminoxybutanoate;
24) 4-[1-cyclohexyl-2-(imidazol-1-yl)ethylidene]aminoxybutanoic acid;
25) 5-[1-cyclohexyl-2-(imidazol-1-yl)ethylidene]aminoxypentanamide;
26) 3-oxa-5-[1-cyclohexyl-2-(imidazol-1-yl)ethylidene]aminoxypentanoic acid;
27) 5-[1-(3,3-dimethylcyclohexyl)-2-(imidazol-1-yl)ethylidene] aminoxypentanoic acid;
28) 5-[1-cyclopentyl-2-(imidazol-1-yl)ethylidene]aminoxypentanoic acid;

29) 5-[1-(2-thienyl)-2-(imidazol-1-yl)ethylidene]aminoxypentanoic acid;
30) ethyl 5-[1-(3-pyridyl)-2-(imidazol-1-yl)ethylidene]aminoxypentanoate;
31) 5-[1-(3-pyridyl)-2-(imidazol-1-yl)ethylidene]aminoxypentanoic acid;
32) 4-[1-(3-pyridyl)-2-(imidazol-1-yl)ethylidene]aminoxybutanoic acid;
33) 5-[1-(3-n-butyloxyphenyl)-2-(imidazol-1-yl)ethylidene]aminoxypentanoic acid;
34) ethyl 5-[1-(3-n-butyloxyphenyl)-2-(imidazol-1-yl)ethylidene]aminoxypentanoate;
35) 6-[1-cyclohexyl-2-(imidazol-1-yl)ethylidene]aminoxyhexanoic acid;
36) 3-oxa-6-[1-cyclohexyl-2-(imidazol-1-yl)ethylidene]aminoxyhexanoic acid;
37) 5-[1-cycloheptyl-2-(imidazol-1-yl)ethylidene]aminoxypentanoic acid;
38) 6-[1-cycloheptyl-2-(imidazol-1-yl)ethylidene]aminoxyhexanoic acid;
39) 5-[1-n-heptyl-2-(imidazol-1-yl)ethylidene]aminoxypentanoic acid;
40) 5-[1-phenyl-2-(imidazol-1-yl)-2-benzylethylidene]aminoxypentanoic acid;
41) 5-[1-cyclohexyl-2-(imidazol-1-yl)-2-benzylethylidene]aminoxypentanoic acid;
42) ethyl 5-[1-phenyl-2-imidazol-1-yl)-2-benzylethylidene]aminoxypentanoate;
43) ethyl 5-[1-cyclohexyl-2-(imidazol-1-yl)-2-benzylethylidene]aminoxypentanoate;
44) 6-[1-phenyl-2-(imidazol-1-yl)-2-benzylethylidene]aminoxyhexanoic acid;
45) 6-[1-cyclohexyl-2-(imidazol-1-yl)-2-benzylethylidene]aminoxyhexanoic acid;
46) 5-[1-(4-fluorophenyl)-2-(imidazol-1-yl)-2-(4-fluorobenzyl)ethylidene] aminoxypentanoic acid;
47) 5-[1-cyclohexyl-2-(imidazol-1-yl)-2-(4-fluorobenzyl)ethylidene]aminoxypentanoic acid; and
48) 3-oxa-5-[1-phenyl-2-(imidazol-1-yl)-2-benzylethylidene]aminoxypentanoic acid;
and the pharmaceutically acceptable salts thereof.

TABLE A

| No. | A | R₁ | T | X | R₂ |
|---|---|---|---|---|---|
| 1 | —CH₂— | Ph | —(CH₂)₃— | bond | OH |
| 2 | —CH₂— | Ph | —(CH₂)₃— | bond | NH₂ |
| 3 | —CH₂— | Ph | —(CH₂)₂— | bond | OEt |
| 4 | —CH₂— | Ph | —(CH₂)₂— | bond | OH |
| 5 | —CH₂— | Ph | —CH₂— | bond | OMe |
| 6 | —CH₂— | (3CF₃)Ph | —CH₂)₃— | bond | OEt |
| 7 | —CH₂— | (3CF₃)Ph | —(CH₂)₃— | bond | OH |
| 8 | —CH₂— | (3Br)Ph | —(CH₂)₃— | bond | OH |
| 9 | —CH₂— | (3CF₃)Ph | —(CH₂)₂— | bond | OH |
| 10 | —CH₂— | (3nBu)Ph | —(CH₂)₃— | bond | OH |
| 11 | —CH₂— | (2OCH₃)Ph | —(CH₂)₃— | bond | OH |
| 12 | —CH₂— | Ph | —CH₂— | —OCH₂— | OEt |
| 13 | —CH₂— | Ph | —CH₂— | —OCH₂— | OH |
| 14 | —CH₂— | (3CF₃)Ph | —CH₂— | —OCH₂— | OH |
| 15 | —CH(CH₃)— | Ph | —(CH₂)₃— | bond | OtBu |
| 16 | —CH(CH₃)— | Ph | —(CH₃)₃— | bond | OH |
| 17 | —CH₂— | Ph | 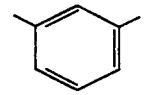 | bond | OH |
| 18 | —(CH₂)₂— | Ph | —(CH₂)₂— | bond | OH |
| 19 | —CH₂— | n-hexyl | —(CH₂)₃— | bond | OH |
| 20 | —CH₂— | cyclohexyl | —(CH₂)₃— | bond | OEt |
| 21 | —CH₂— | cyclohexyl | —(CH₂)₃— | bond | OtBu |
| 22 | —CH₂— | cyclohexyl | —(CH₂)₃— | bond | OH |
| 23 | —CH₂— | cyclohexyl | —(CH₂)₂— | bond | OEt |
| 24 | —CH₂— | cyclohexyl | —(CH₂)₂— | bond | OH |
| 25 | —CH₂— | cyclohexyl | —(CH₂)₃— | bond | NH₂ |
| 26 | —CH₂— | cyclohexyl | —CH₂— | —OCH₃— | OH |
| 27 | —CH₂— | (3,3-di-Me) cyclohexyl | —(CH₂)₃— | bond | OH |
| 28 | —CH₂— | cyclopentyl | —(CH₂)₃— | bond | OH |
| 29 | —CH₂— | 2-thienyl | —(CH₂)₃— | bond | OH |
| 30 | —CH₂— | 3-pyridyl | —(CH₂)₃— | bond | OEt |
| 31 | —CH₂— | 3-pyridyl | —(CH₂)₃— | bond | OH |
| 32 | —CH₂— | 3-pyridyl | —(CH₂)₂— | bond | OH |
| 33 | —CH₂— | (3nBuO)Ph | —(CH₂)₃— | bond | OH |
| 34 | —CH₂— | (3nBuO)Ph | —(CH₂)₃— | bond | OEt |
| 35 | —CH₂— | cyclohexyl | —(CH₂)₄— | bond | OH |
| 36 | —CH₂— | cyclohexyl | —(CH₂)₂— | —OCH₂— | OH |
| 37 | —CH₂— | cycloheptyl | —(CH₂)₃— | bond | OH |
| 38 | —CH₂— | cycloheptyl | —(CH₂)₄— | bond | OH |
| 39 | —CH₂— | n-heptyl | —(CH₂)₃— | bond | OH |
| 40 | —CH(PhCH₂)— | Ph | —(CH₂)₃— | bond | OH |
| 41 | —CH(PhCH₂)— | cyclohexyl | —(CH₂)₃— | bond | OH |
| 42 | —CH(PhCH₂)— | Ph | —(CH₂)₃— | bond | OEt |
| 43 | —CH(PhCH₂)— | cyclohexyl | —(CH₂)₃— | bond | OEt |
| 44 | —CH(PhCH₂)— | Ph | —(CH₂)₄— | bond | OH |
| 45 | —CH(PhCH₂)— | cyclohexyl | —(CH₂)₄— | bond | OH |
| 46 | —CH(4-F—PhCH₂)— | 4-F—Ph | —(CH₂)₃— | bond | OH |
| 47 | —CH(4-F—PhCH₂)— | cyclohexyl | —(CH₂)₃— | bond | OH |

TABLE A-continued

| No. | A | R₁ | T | X | R₂ |
|---|---|---|---|---|---|
| 48 | —CH(PhCH₂)— | Ph | —CH₂— | —OCH₂— | OH |

In the above table Ph means phenyl; Me means methyl; Et means ethyl; and Bu means butyl.

The compounds of the invention and the salts thereof can be obtained by a process comprising:

a) reacting an oxime of formula (II) or a salt thereof

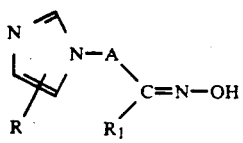
(II)

wherein R, A and R₁ are as defined above, with a compound of formula (III)

Y—CH₂—T—X—COR₂ (III)

wherein T, X and R₂ are as defined above and Y is a leaving group; or b) reacting an oxime of formula (II) as defined above or a salt thereof with a lactone of formula (IV)

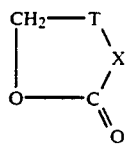
(IV)

wherein T and X are as defined above, thus obtaining a compound of formula (I) in which R₂ is —OH; or c) reacting a compound of formula (V)

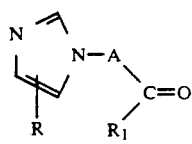
(V)

wherein R, A and R₁ are as defined above, with a compound of formula (VI)

H₂N—O—CH₂—T—X—COR₂ (VI)

wherein T, X and R₂ are as defined above; or d) reacting a compound of formula (V), as defined above, with a compound of formula (VII)

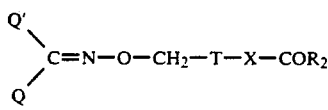
(VII)

wherein T, X and R₂ are as defined above and each of Q and Q' is independently hydrogen, lower alkyl or phenyl; or e) reacting a compound of formula (VIII) or a salt thereof

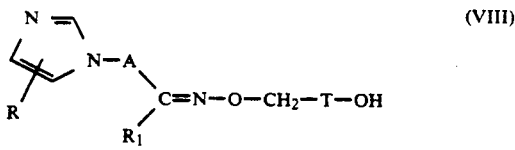
(VIII)

wherein R, R₁, A and T are as defined above, with a compound of formula (IX)

Y—CH₂—COR₂ (IX)

wherein Y and R₂ are as defined above, thus obtaining a compound of formula (I) wherein X is a —O—CH₂— group; and if desired, converting a compound of formula (I) into another compound of formula (I), and/or, if desired converting a compound of formula (I) into a salt thereof, and/or, if desired, converting a salt of a compound of formula (I) into a free compound, and/or, if desired, separating a mixture of isomers of a compound of formula (I) into the single isomers, and/or, if desired, altering by isomerization on the oxime double bond the ratio of E- and Z-isomers of a compound of formula (I) in a mixture thereof so as to obtain a different ratio of such isomers, and/or, if desired, converting by isomerization on the oxime double bond a pure E-isomer of a compound of formula (I) either into a pure Z-isomer thereof or into a mixture of E- and Z-isomers thereof; and/or if desired converting by isomerization on the oxime double bond a pure Z-isomer of a compound of formula (I) either into a pure E-isomer or into a mixture of E- and Z-isomers thereof.

A salt of a compound of formula (II) is for example an alkali metal salt, in particular a sodium or lithium salt. A salt of a compound of formula (II) may be obtained according to known methods, for example a compound of formula (II) can be reacted with an alkali metal hydride, preferably NaH, in an inert organic solvent, e.g. dimethylformamide.

The leaving group Y in a compound of formula (III) is for example an halo group, in particular a chloro or bromo group, or a residue of an active ester group, in particular mesyl or tosyl.

The reaction of a compound of formula (II), or a salt thereof, with a compound of formula (III) can be carried out according to known methods, for example in the presence of an inert reaction organic solvent e.g. dimethylformamide, dimethylsulfoxide, tert. butanol or benzene, and by addition of an appropriate basic agent e.g. an alkali metal carbonate, in particular sodium carbonate, or sodium hydride or potassium tert. butylate, at a temperature ranging from about 0° C. to reflux temperature.

The reaction of a compound of formula (II) or a salt thereof, as defined above, with a compound of formula (IV) may be performed according to known methods. For example such reaction can be carried out by following the same reaction conditions described as to the reaction of a compound of formula (II), or a salt thereof, with a compound of formula (III). The reaction of a carbonyl compound of formula (V) with an aminooxi derivative of formula (VI) can be carried out for example, by dissolving the carbonyl compound in a reaction inert solvent e.g. water, a lower alkanol in particular ethanol, dioxane, tetrahydrofuran, an aromatic hydrocarbon in particular benzene, toluene or xylene, or mixtures of such solvents, and by adding an appropriate basic agent, for example an alkali metal hydroxide in particular sodium or potassium hydroxide, a carbonate or hydrogen carbonate in particular the sodium and potassium ones, or an organic basic agent e.g. a tertiary amine or pyridine.

When one or both of Q and Q' in a compound of formula (VII) is lower alkyl, it is for example $C_1-C_4$ alkyl in particular methyl or ethyl.

Also the reaction of a compound of formula (V) with a compound of formula (VII) can be carried out according to known methods. For example such reaction can be performed in an inert reaction solvent e.g. acetonitrile or acetic acid, and if required in the presence of a mineral acid e.g. sulphuric or hydrochloric acid, at temperatures ranging from room temperature to reflux temperature.

A salt of a compound of formula (VIII) is for example an alkali metal salt, in particular a sodium or lithium salt.

The leaving group Y in a compound of formula (IX) is for example a halo group, in particular a chloro or bromo group, or a residue of an active ester group, in particular mesyl or tosyl.

The reaction of a compound of formula (VIII), or a salt thereof, with a compound of formula (IX) can be carried out by following the same reaction conditions described above as to the reaction of a compound of formula (II), or a salt thereof, with a compound of formula (III).

The conversion of a compound of formula (I) into another compound of formula (I) can be carried out by methods known in themselves. For example, a compound of formula (I) containing an esterified carboxy group can be converted into the corresponding free carboxylic acid by known methods. In particular a compound of formula (I) in which $R_2$ is an $OR_3$ group wherein $R_3$, being as defined above, is other than hydrogen can be converted by acidic or alkaline hydrolysis into the respective free carboxylic acid. The reaction is preferably carried out at temperatures ranging from about $-5°$ C. to about $50°$ C.

A compound of formula (I) containing a free carboxy group, such as a compound of formula (I) in which $R_2$ is hydroxy, can be converted into a corresponding esterified carboxy derivative, e.g. a compound of formula (I) in which $R_2$ is an $—OR_3$ group, wherein $R_3$, being as defined above, is other than hydrogen. Such esterification reaction can be carried out according to known methods, preferably via an intermediate reactive derivative of the carboxylic acid, which may be isolated or not, by reaction with the appropriate alcohol of formula $R_3OH$, in which $R_3$ being as defined above, is other than hydrogen. The reaction can be carried out in a customary solvent e.g. benzene or toluene, or in the presence of an excess of the alcohol itself of formula $R_3OH$.

The temperature reaction may range from about 10° C. to about 50° C. Intermediate reactive derivatives of the carboxylic acid may be for example acidic halides, e.g. the chloride, mixed anhydrides e.g. ethoxycarbonyl or tert. butyloxy anhydrides, or a suitable reactive intermediate obtained in situ e.g. by reaction with a diimide e.g., dicyclohexylcarbodiimide, or carbonyl diimidazole.

A compound of formula (I) wherein $R_2$ is hydroxy, i.e. containing a free carboxy group, can be converted into a corresponding compound of formula (I) wherein $R_2$ is a $—NR_3 R_4$ group, in which $R_3$ and $R_4$ are as defined above, according to known methods; preferably via an intermediate reactive derivative thereof, which can be isolated or not.

Intermediate reactive derivatives may be active esters e.g. $NO_2$-phenyl esters, or N-hydroxysuccinimide esters, acid halides, preferably chloride, mixed anhydrides e.g. ethoxycarbonyl or tert-butylcarbonyl anhydrides, or the reactive intermediates obtained in situ by reaction of the acid with dicyclohexylcarbodiimide or carbonyldiimidazole.

For example, a reactive intermediate as defined above, which can be obtained following conventional ways, as those usually employed in the synthesis of peptides, is reacted with ammonia or an appropriate amine in a customary solvent or with an excess of the amine itself at temperatures ranging from about $-10°$ C. to about $50°$ C.

The optional salification of a compound of formula (I) as well as the conversion of a salt into the free compound and the separation of a mixture of isomers into the single isomers may be carried out by conventional methods.

For example the separation of a mixture of geometric isomers, e.g. Z- and E-isomers, may be carried out by fractional crystallization from a suitable solvent or by chromatography, either column chromatography or high pressure liquid chromatography.

The optional isomerization on the oxime double bond in a compound of formula (I), which is an equilibrium reaction, can be performed according to known methods; preferably in the presence of a mineral acid e.g. hydrochloric acid and/or by heating.

The oximes of formula (II) can be obtained according to know methods. For example a') by reaction of a compound of formula (V), as defined above, with hydroxylamine or an acid addition salt thereof, e.g. the sodium or potassium salt, or b') by reaction of an oxime of formula (X)

wherein Y, A and $R_1$ are as defined above, with imidazole, $C_1-C_4$ alkyl imidazole or a salt thereof, e.g. following for example the procedure in Arzneim. Forsch./Drug Res., 29(II), 1510-13, (1979).

In view of the oxime double bond, also an oxime of formula (II) may be obtained either as pure Z or E isomer or as a mixture thereof. Also an oxime of formula (II), if desired, can be submitted to the same isomerizations on the oxime double bond described above as to a compound of formula (I), according to known methods. Similarly, a mixture of Z and E isomers of an oxime of formula (II) can be separated into the single isomers by following customary methods.

The compounds of formula (III), (IV) and (V) are either known compounds or can be obtained by known methods from known compounds. Also the compounds of formula (VI) are either known compounds or can be obtained from known compounds by following known methods, e.g. those described in Tetrahedron (1967), 23, 4441, or in general described in Organic Functional Group Preparation, by S. R. Sandler and W. Karo, Vol. III, chapter X, Academic Press, (1972).

The compounds of formula (VII) can be obtained by reaction of a known compound of formula (XI)

(XI)

wherein Q and Q' are as defined above, with a compound of formula (VI) as defined above, by following the same reaction procedures described above under process c). Alternatively a compound of formula (VII) can be obtained from a compound of formula (XI), via the corresponding oxime of formula (XII)

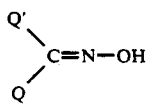
(XII)

wherein Q and Q' are as defined above, by reaction either with a compound either of formula (III) or of formula (IV) by following the same reaction conditions described above under processes a) and b).

The compounds of formula (VIII) can be obtained from known compounds by following procedures similar to those described under processes a), b), c) and d) above.

When in the compounds of the invention and in the intermediate products thereof groups are present which need to be protected during the reactions reported above, the groups can be protected in conventional way before the reaction takes place and then deprotected after its end, according to well known methods.

PHARMACOLOGY

We have found that the compounds of formula (I), and the pharmaceutically acceptable salts thereof are selective inhibitors of thromboxane $A_2$ ($TxA_2$) synthesis and are therefore useful in the treatment of diseases related in particular to an enhancement of $TxA_2$ synthesis in mammals, including humans.

The compounds of formula (I) were for example tested for their ability to inhibit $TxA_2$ Synthase activity (as reflected by $TxB_2$ generated in whole blood during clotting or in isolated glomeruli) in vitro in the rat.

The in vitro experiments were carried out as follows: The effect of the compounds on $TxA_2$ synthesis was evaluated in serum and in glomeruli isolated from kidney cortex of reduced renal mass rats (RRM). Ablation of >70% of renal mass in the rat results in hypertension, proteinuria and glomerular sclerosis of the remnant kidney. Rats with a remnant kidney have increased excretion of thromboxane in the urine when compared with normal rats (Purkerson et al., Proc. Natl. Acad. Sci. USA 82, 193, 1985).

Blood was withdrawn from the abdominal aorta of the animals under light ether anesthesia. The blood was immediately divided in portions of 0.5 ml and distributed in glass tubes each containing a concentration of the test compounds or of the reference compounds, i.e. Dazoxiben, which is thromboxane synthase inhibitor (Randall et al.-Thromb. Res. 23, 145, 1981) and Acetylsalicylic acid (ASA), which is cyclooxygenase inhibitor.

Samples were then allowed to clot for 1 h at 37° C., centrifuged at 3000 rpm for 10 min, serum collected and stored at −20° C. until assayed. $TxB_2$ levels were determined by RIA according to previously described procedures [Patrono et al.-Thromb. Res. 17, 3/4, 317, 1980] using highly specific antibody.

The isolation of glomeruli was performed as previously described [Patrignani et al., -J. Pharm. Exp. Ther. 228, 2, 472, 1984].

The isolated glomeruli of 4 rats were pooled, suspended in modified Krebs buffer (pH 7.3) and divided into portions of 1 ml each containing a concentration of the test compounds or of the reference compounds.

The $TxA_2$ synthesis was induced by incubating the glomeruli under shaking at 37° C. for 1 h. At that time the incubation was stopped by centrifugation at +4° C., the supernatant collected and stored at −20° C. until assayed by RIA.

The compounds of the invention showed remarkable activity in the above tests.

In particular for example, the compounds of the invention (Z)-5-[1-cyclohexyl-2-(imidazol-1-yl)-ethylidene]aminoxypentanoic acid (internal code FCE 26398), (±) (Z)-5-[1-phenyl-2-(imidazol-1-yl)-2-benzylethylidene]aminoxypentanoic acid (FCE 27108) and (±) (E)-5-[1-phenyl-2-(imidazol-1-yl)-2-benzylethylidene]aminoxypentanoic acid (FCE 27109), were found to exhibit a marked inhibitory activity on $TxA_2$ synthesis significantly more potent than that of reference compounds Dazoxiben and ASA. These results are summarized in Table 1.

TABLE 1

| | In vitro effects on $T \times B_2$ production in whole blood and glomeruli of RRM rats. [Data are expressed as $IC_{50}$ (M) and limits for p = 0.95]. | |
|---|---|---|
| Compound | Whole Blood (n = 8) | Glomeruli (n = 6) |
| FCE 26398 | $1.9 \times 10^{-8}$ $(1.3-2.8 \times 10^{-8})$ | $3.6 \times 10^{-8}$ $(2.8-5.5 \times 10^{-8})$ |
| FCE 27108 | $2.30 \times 10^{-8}$ $(0.64-4.96 \times 10^{-8})$ | — |
| FCE 27109 | $4.83 \times 10^{-8}$ $(2.32-8.65 \times 10^{-8})$ | — |
| Dazoxiben | $1.2 \times 10^{-6}$ $(0.70-1.9 \times 10^{-6})$ | $1.7 \times 10^{-7}$ $(1.2-2.2 \times 10^{-7})$ |
| ASA | $4.2 \times 10^{-5}$ $(3.1-5.6 \times 10^{-5})$ | $1.4 \times 10^{-4}$ $(1.1-1.7 \times 10^{-4})$ |

Wherein n is the number of replications.

The compounds of the invention, being able to inhibit selectively the formation of $TxA_2$, can be used as vasodilatory and antiaggregant agents, for example in all the cases of thrombosis, peripheral vasculopathies and coronary artery disease. In fact inhibition of $TxA_2$ production reduces the probability of thrombi formation and of vasoconstriction with consequent ischemic events and leaving unaltered (or increasing) $PGI_2$ production, improves vasodilation, tissue blood supplies and protects the vessel wall.

Moreover the compounds of the invention were tested for $TxA_2$ antagonism in a binding assay in washed human platelets, using as radiolabelled ligand [$^3$H]-SQ 29,548.

The experiments were carried out as follows: Blood from healthy volunteers of both sexes who had no taken any medication for at least 10 days is collected into one-tenth volume of acid citrate dextrose containing indomethacin (28 μM). Platelet rich plasma (PRP), obtained by centrifugation of the blood at 200×g for 20 min, is washed twice (1000×g for 10 min). The platelets are then resuspended in Tyrode-Hepes buffer (pH 7.4) to a final concentration of $5-10 \times 10^{-8}$ cells/ml and incubated for 0-60 min at 25° with [$^3$H]-SQ 29,548 (5 nM). For displacement experiments various concentrations ($10^{-9} - 10^{-4}$M) of competing ligands were added and incubated for 30 min at 25° C.

Non-specific binding was determined in the presence of 50 μM U46619 and was approximately 5% of total binding of [$^3$H]-SQ 29,548. After the incubation, 4 ml of ice-cold TRIS-HCL buffer (10 mM, pH 7.4) was added to each tube and the reaction mixture was immediately filtered by suction through a Whatman GE/C glass filter disc which was washed 2 times with ice-cold TRIS-HCl (4 ml) and counted for radioactivity by a Packard-β-counter.

The binding data were analysed by computerized non-linear curve fitting using the Ligand program and expressed as $IC_{50}$ In Table II, as an example, the result obtained with the compound of the invention (±) (E)-5-[1-phenyl-2-imidazol-1-yl)-2-benzylethylidene]aminoxypentanoic acid (code number FCE 27109) in the binding test is compared to that obtained with the reference standard compound Sulotroban (BM 13177) [DE-A-2,809,377].

This result shows that the compound of the invention FCE 27109, besides being active as $TxA_2$ synthase inhibitor, has also a good affinity for the receptor better than that showed by the known compound Sulotroban (BM 13177), which on the other hand is devoid of $TxA_2$ synthase inhibitory activity.

TABLE II

| $^3$H SQ 29.548 binding displacement (washed human platelets).$IC_{50}$ (M). | |
|---|---|
| BM 13177 | $7.3 \times 10^{-6}$ |
| FCE 27109 | $1.9 \times 10^{-7}$ |

Being the compounds of the present invention both $TxA_2$ synthase inhibitors and $PGA_2(TxA_2)$antagonists in the platelets on the basis of the state of the art, as reported e.g. in J. Clin. Invest. 80, 1435 (1987) and in Adm. Prostaglandins, Tromboxanes, Leukotrienes Res. Vol. 17 (1987) p. 49, these compounds result particularly suitable for the treatment of a disease state in which an enhancement of $TxA_2$ synthesis exerts a pathogenic effect, for instance in those mentioned above.

Another use of the compounds of the invention is for the treatment of migraine. As is known, for example, in the case of migraine it has been demonstrated a diffused vasoconstriction induced by platelet $TxA_2$ overproduction [J. Clin. Pathol. (1971), 24, 250; J. Headache (1977) 17, 101]. A platelet overproduction of $TxA_2$ and MDA (malondialdehyde) in diabetes mellitus has been demonstrated and correlated with microcirculatory defects in the illness [Metabolism (1979) 28, 394; Eu. J. Clin. Invest. (1979) 9, 223; Thrombosis Haemost. (1979), 42, 983; J. Lab. Clin. Med. (1981) 97, 87]. Therefore, the compounds of the invention can be used in the treatment of diabetes, in particular, diabetic microangiopathy.

Moreover, the compounds of the invention can be used as anti-inflammatory agents. As is known, for example, fluid obtained from carrageenin-induced granuloma converts arachidonic acid into $TxA_2$ in vitro and $TxA_2$ levels are increased in the synovial fluid of rheumatoid arthritis patients and in the fluid of carrageenin-induced inflammation in rats [Prostaglands (1977), 13, 17; Scand. J. Rheum. (1977), 6, 151]. Recently it has been also demonstrated that an overproduction of $TxA_2$ is involved in the pathogenesis of hypertension and that a specific inhibitor of $TxA_2$ production may be employed in hypertension [Eu. J. Pharmacol. (1981), 70, 247]. In fact the compounds of the invention can be used as hypotensive agents.

For example an increased $TxA_2$ synthesis and decreased prostacyclin synthesis are reported in pregnancy-induced hypertension [Am. J. Obstet:Gynecol. (1987), 157, 325; Hypertension (1988), 11, 550]. Treatment with thromboxane synthase inhibitors is therefore useful in this pathology.

Furthermore it has been shown a role of $TxA_2$ in the pathogenesis of ulcerative disorders of the stomach in accordance with its powerful gastric vasoconstrictory activity, so that also in this field a $TxA_2$ inhibitor is useful [Nature (1981), 202, 472]. In fact the compounds of the invention are indicated for the treatment of peptic ulcers.

The compounds of the invention can be also antitumoral agents. It is known, for example, that a selective inhibition of $TxA_2$ synthesis has been demonstrated to reduce the number of lung metastases and to slow down tumor growth [Nature (1982), 295, 188].

In view of the correlation between $TxA_2$ synthesis and calcium transport, recently showed by some authors, specific $TxA_2$ synthetase inhibitors, such as the compounds of the invention, can also find use in the treatment of osteoporosis, e.g. post-menopausal osteoporosis [Prostaglandins (1981), 21, 401].

Moreover the compounds of the invention are indicated for the treatment of angina pectoris and heart failure. In this respect, it is known, for example, that high levels of $TxB_2$ have been found in patients with Prinzmetal's angina [Prostaglandins and Med. (1979), 2, 243] and in patients with recurrent angina attacks [Sixth Intern. Congress on Thrombosis, Monte Carlo October, 1980 Abs No. 140].

The platelet antiaggregatory activity of the compounds of the invention was evaluated in vitro and in vivo, for example, according to the modified methods of Born [Born G. V. R., Nature 194, 927 (1962)] and Silver [Silver M. J., Science 183, 1085 (1974)].

The compounds of this invention were found in vitro to have inhibitory activity on platelet aggregation induced by collagen or ADP (adenosine-5'-diphosphate) in platelet rich plasma of guinea pig [Dunkin Hantley Iva: PDH (SPF) Ivanovas GmBH, Germany].

Therefore the compounds of the invention may be useful in preventing or reducing platelet loss during extracorporeal circulation; for example during coronary artery bypass and graft procedures or during kidney dialaysis. It has been moreover shown that circulatory shock, for example endotoxic and haemorragic shock, is associated with increased $TxA_2$ synthesis so that the compounds of the invention can be useful in these pathologies. Moreover, the compounds of the present invention can also be useful for the treatment of bronchial hyperreactivity in the therapy of asthma.

A role for $TxA_2$ in asthma can be inferred on the basis of its bronchoconstrictory activity in experimental animal models [Br. J. Pharmacol. (1984), 82 (3) 565]. An inhibitory activity of bronchospasm induced by Platelet Activating Factor (PAF) in rats is also reported, e.g. for the $TxA_2$ synthetase inhibitors described in GB-B-2205494.

The compounds of the present invention can also find use in the treatment of nephropathies e.g. forms of glomerulonephritis, diabetic nephropathy or nephropathies secondary to systemic lupus erithematous (SLE), and in the prevention and/or treatment of Cyclosporin A-induced nephrosis. Accordingly the compounds of this invention can also be used for preventing and/or treating toxemia during pregnancy, typically preeclampsia, eclampsia and preeclamptic (eclamptic, eclamptogenic) toxemia.

Recently a positive correlation between enhanced intrarenal synthesis of $TxA_2$ and the progression of chronic glomerular disease has been demonstrated in different animal models of immune and non-immune renal damage and in humans [J. Clin. Invest. (1985) 75, 94, J. Clin. Invest. (1985), 76, 1011].

Accordingly, the $TxA_2$ synthase inhibitors recently described e.g. in GB-B-2205240 were found to be active in reducing proteinuria and creatinine serum levels in the doxorubicin induced nephrosis in rats and in reducing proteinuria and increasing the glomerular filtration rate (GFR) in the spontaneous focal glomureulosclerosis in the Milan Normotensive Strain (MNS) rats.

The compounds of the invention may be also used to inhibit the renal and cardiac transplant rejection. In fact after transplantation increased urinary $TxB_2$ excretion or whole blood $TxA_2$ synthesis have been reported both in man and rats [Lancet (1981), ii, 431; Transplantation (1987) 43, 346].

Another use of the compounds of the present invention is in the treatment of hyperlipidaemia, namely hypercholesterolaemia and hypertriglyceridaemia secondary to nephrotic syndrome.

Hyperlipidaemia is a common feature of nephrotic syndrome in man [New Engl. J. Med. (1983) 312 (24) 1544] and in addition elevated triglycerides and cholesterol levels are reported in animal models such as doxorubicin induced nephrotic syndrome [Expt. Mol. Pathology (1983), 39, 282]; elevated urinary albumin excretion has been suggested as the pathogenetic mechanisms [Kidney International (1987), 32, 813]. Also $TxA_2$ synthase inhibitors recently described in GB-B-2205240, e.g. proved to be active in reducing cholesterol and triglycerides in aged Milan Normotenisve Strain rats and in reducing triglycerides in doxorubicin treated rats.

It has also been shown that in cholesterol fed rabbit, an animal model of diet induced atherosclerosis, arachidonic acid metabolism is an important factor in early lesion development. In particular a shift in metabolism from $TxA_2$ to $PGE_2$ may suppress lesion development (i.e. atheromatous plaque) in hypercholesterolemia.

The compounds of invention can be therefore used in this pathology.

The compounds of the invention can also be used in association with thrombolytic agents (e.g. tPA, Streptokinase, pro-Urokinase) in order to reduce the dose of the latter required in thrombolytic therapy, and to lower the incidence of reocclusion and possibly haemorrage. A further application of the compounds of the invention is the prevention and/or treatment of restenosis after percutaneous transluminal angioplasty.

The toxicity of the compounds of the invention is negligible, therefore they can be safely used in therapy. Mice and rats which had been deprived of food for nine hours were treated orally with single administrations of increasing doses of compounds of the invention, then housed and normally fed. The orientative acute toxicity ($LD_{50}$) was assessed on the seventh day after the treatment.

In view of their high activity and low toxicity, the compounds of the invention can be safely used in medicine. The therapeutic regimen for the different clinical syndromes must be adapted to the type of pathology, taking into account, as usual, also the route of administration, the form in which the compound is administered and the age, weight and conditions of the subject involved. The oral route is employed, in general, for all conditions requiring such compounds. Preference is given to intravenous injection or infusion for the treatment of acute pathological states.

For maintenance regimens the oral or parenteral, e.g. intramuscular, route is preferred.

The dosage level suitable for oral administration to adult humans of the compounds of the invention e.g. (E)($\pm$)5-[1-phenyl-2-(imidazol-1-yl)-2-benzylethylidene]aminoxypentanoic acid may range from about 50 mg to about 500 mg per dose, 1 to 3 times a day.

Of course, these dosage regimens may be adjusted to provide the optimal therapeutic response.

The nature of the pharmaceutical compositions containing the compounds of this invention in association with pharmaceutically acceptable carriers or diluents will, of course, depend upon the desired route of administration. The compositions may be formulated in the conventional manner with the usual ingredients. For example, the compounds of the invention may be administered in the form of aqueous or oily solutions, or suspensions tablets, pills, gelatine capsules, syrups, drops or suppositories.

Thus, for oral administration, the pharmaceutical compositions containing the compounds of this invention are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpirrolidone; disaggregating agents, such as starches, alginic acid, alginates, sodium starch glycolate; effervescing mixtures; dyestuffs; sweeteners; wetting agents, such as lecithin, polysorbates, laurylsulphates; and in general, non-toxic and pharmacologically inactive substances used in pharmaceutical formulations. Said pharmaceutical preparations may be manufactured in known manner, for example by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride. The solutions for intravenous injection or infusion may contain as carrier, for example, sterile water or preferably they may be in the form of sterile aqueous isotonic saline solutions.

The suppositories may contain together with the active compound a pharmaceutically acceptable carrier e.g. cocoa-butter, polyethylene glycol, a polyoxyethylene sorbitan fatty acid ester surfactant or lecithin. The following examples illustrate but do not limit the present invention.

EXAMPLE 1

To a stirred mixture of 5 g (0.025 moles) of (Z)-1-phenyl-2-(imidazol-1-yl)ethanone oxime and 20 ml of dimethylformamide, 0.9 g (0.03 moles) of sodium hydride dispersion 80% are added portionwise at room temperature. Upon completion, stirring is continued till hydrogen evolution stops. Then 4.74 ml (0.03 moles) of ethyl 5-bromopentanoate are added dropwise at room temperature and stirring is continued for 6 hours. The reaction mixture is evaporated under vacuum, diluted with water and extracted with chloroform. The organic phase dried over $CaCl_2$ is evaporated to dryness. The residue is purified by column chromatography over silica gel (eluant: chloroform/methanol=97/3). The pure fractions are collected and evaporated, yielding 4.41 g (53%) of ethyl (Z)-5-[1-phenyl-2-(imidazol-1-yl)ethylidene]aminoxypentanoate.

| NMR ($CDCl_3$): | |
|---|---|
| 1.15 | (3H, t, —COOCH$_2$C$\underline{H}_3$) |
| 1.6–1.9 | (4H, m, —OCH$_2$C$\underline{H}_2$C$\underline{H}_2$CH$_2$—) |
| 2.35 | (2H, m, —C$\underline{H}_2$COO—) |
| 4.13 | (2H, q, —COOC$\underline{H}_2$CH$_3$) |
| 4.27 | (2H, m, —OC$\underline{H}_2$CH$_2$CH$_2$CH$_2$—) |
| 5.16 | (2H, s, —C$\underline{H}_2$—N=) |
| 6.89 | (1H, dd, C$\underline{H}$ at 5 position of imidazole ring) |
| 6.98 | (1H, dd, C$\underline{H}$ at 4 position of imidazole ring) |
| 7.25–7.70 | (6H, m, —N=C$\underline{H}$—N— + phenyl ring) |

By the same procedure, starting from either an (E) or (Z) oxime of formula (II) or a mixture thereof, the following compounds can be prepared:

ethyl (Z)-4-[1-phenyl-2-(imidazol-1-yl)ethylidene]aminoxybutanoate:
Microanalysis: Found: C 64.03; H 6.80; N 13.01 Calculated for $C_{17}H_{21}N_3O_3$: C 64.74; H 6.71; N 13.32

| NMR ($CDCl_3$): | |
|---|---|
| 1.24 | (3H, t, —COOCH$_2$C$\underline{H}_3$) |
| 2.07 | (2H, m, —OCH$_2$C$\underline{H}_2$CH$_2$—) |
| 2.40 | (2H, t, —OCH$_2$CH$_2$C$\underline{H}_2$COO—) |
| 4.12 | (2H, q, —COOC$\underline{H}_2$CH$_3$) |
| 4.30 | (2H, t, —OC$\underline{H}_2$CH$_2$CH$_2$—) |
| 5.15 | (2H, s, —C$\underline{H}_2$—N=) |
| 6.88 | (1H, bs, C$\underline{H}$ at 5 position of imidazole ring) |
| 6.98 | (1H, bs, C$\underline{H}$ at 4 position of imidazole ring) |
| 7.30–7.60 | (6H, m, —N=C$\underline{H}$—N— + phenyl ring) | methyl (Z)-3-[1-phenyl-2-(imidazol-1-yl)ethylidene]aminoxypropanoate:
Microanalysis: Found: C 61.81; H 6.05; N 14.35 Calculated for $C_{15}H_{17}N_3O_3$: C 62.71; H 5.96; N 14.62

| NMR ($CDCl_3$): | |
|---|---|
| 2.80 | (2H, t, —C$\underline{H}_2$COOCH$_3$) |
| 3.70 | (3H, s, —COOC$\underline{H}_3$) |
| 4.54 | (2H, t, —OC$\underline{H}_2$CH$_2$—) |
| 5.14 | (2H, s, —C$\underline{H}_2$—N=) |
| 6.88 | (1H, t, C$\underline{H}$ at 5 position of imidazole ring) |
| 6.98 | (1H, t, C$\underline{H}$ at 4 position of imidazole ring) |
| 7.30–7.60 | (6H, m, —N=C$\underline{H}$—N— + phenyl ring) | ethyl (Z)-5-[1-(3-trifluoromethylphenyl)-2-(imidazol-1-yl)ethylidene]aminoxypentanoate:

| NMR ($CDCl_3$): | |
|---|---|
| 1.26 | (3H, t, —COOCH$_2$C$\underline{H}_3$) |
| 1.6–1.19 | (4H, m, —OCH$_2$C$\underline{H}_2$C$\underline{H}_2$CH$_2$—) |
| 2.38 | (2H, m, —C$\underline{H}_2$COO—) |
| 4.15 | (2H, q, —COOC$\underline{H}_2$CH$_3$) |
| 4.34 | (2H, m, —OC$\underline{H}_2$CH$_2$CH$_2$CH$_2$—) |
| 5.24 | (2H, s, —C$\underline{H}_2$—N=) |
| 6.91 | (1H, bs, C$\underline{H}$ at 5 position of imidazole ring) |
| 7.04 | (1H, bs, C$\underline{H}$ at 4 position of imidazole ring) |
| 7.40–7.80 | (4H, m, phenyl ring) |
| 7.87 | (1H, bs, —N=C$\underline{H}$—N—) | ethyl (Z)-5-[1-(3-n-butyloxyphenyl)-2-(imidazol-1-yl)ethylidene]aminoxypentanoate:
Microanalysis: Found: C 65.32; H 7.86; N 9.93 Calculated for $C_{22}H_{31}N_3O_4$: C 65.81; H 7.78; N 10.47

| NMR ($CDCl_3$): | |
|---|---|
| 0.95 | (3H, t, C$\underline{H}_3$—CH$_2$—CH$_2$—) |
| 1.23 | (3H, t, —COO—CH$_2$—C$\underline{H}_3$) |
| 1.4–1.8 | (8H, m, —O—CH$_2$—C$\underline{H}_2$—C$\underline{H}_2$—CH$_2$—COO— + CH$_3$—C$\underline{H}_2$—C$\underline{H}_2$—CH$_2$—O—) |
| 2.34 | (2H, m, —C$\underline{H}_2$—COO—) |
| 3.8–4.3 | (6H, m, —COO—C$\underline{H}_2$—CH$_3$ + —OC$\underline{H}_2$—CH$_2$—CH$_2$—CH$_3$ + —OC$\underline{H}_2$—CH$_2$—CH$_2$—CH$_2$—COO—) |
| 5.12 | (2H, s, —C$\underline{H}_2$—N=) |
| 6.8–7.5 | (7H, m, phenyl ring + imidazole ring) | ethyl (Z)-5-[1-(3-pyridyl)-2-(imidazol-1-yl)ethylidene]aminoxypentanoate:
Microanalysis: Found: C 60.18; H 6.84; N 16.64 Calculated for $C_{17}H_{22}N_4O_3$: C 61.80; H 6.71; N 16.96

| NMR ($CDCl_3$): | |
|---|---|
| 1.22 | (3H, t, —COOCH$_2$—C$\underline{H}_3$) |
| 1.75 | (4H, m, —OCH$_2$—C$\underline{H}_2$—C$\underline{H}_2$—CH$_2$—) |
| 2.35 | (2H, m, —C$\underline{H}_2$—COO—) |
| 4.10 | (2H, q, —COOC$\underline{H}_2$—CH$_3$) |
| 4.29 | (2H, m, —OC$\underline{H}_2$—CH$_2$—CH$_2$—CH$_2$—) |
| 5.17 | (2H, s, —C$\underline{H}_2$—N=) |
| 6.8–7.8 | (5H, m, C$\underline{H}$ at 4 and 5 positions of pyridine ring + imidazole ring) |
| 8.57 | (1H, dd, C$\underline{H}$ at 6 position of pyridine ring) |

| NMR (CDCl$_3$): | |
|---|---|
| 8.78 | (1H, dd, C$\underline{H}$ at 2 position of pyridine ring) | and analogously:
ethyl (Z)-3-oxa-5-[1-phenyl-2-(imidazol-1-yl)ethylidene]aminoxypentanoate;
tert-butyl(±)(E)-5-[1-phenyl-2-(imidazol-1-yl)-2-methylethylidene]aminoxypentanoate;
ethyl (E)-5-[1-cyclohexyl-2-(imidazol-1-yl)ethylidene]aminoxypentanoate; and
tert-butyl (E)-5-[1-cyclohexyl-2-(imidazol-1-yl)ethylidene]aminoxypentanoate.

EXAMPLE 2

By proceeding according to the method described in Example 1 and starting from the appropriate oxime of formula (II) as a mixture of Z- and E-isomers, after separation by column chromatography over silica gel of the crude reaction mixture, using as eluant chloroform and methanol in different ratios, the following compounds can be obtained either as (Z) or (E) isomer:
tert-butyl(±)(E)-5-[1-phenyl-2-(imidazol-1-yl)-2-methylethylidene]aminoxypentanoate:

| NMR (CDCl$_3$): | |
|---|---|
| 1.42 | (9H, s, —(C$\underline{H}_3$)$_3$) |
| 1.60 | (4H, m, —OCH$_2$C$\underline{H}_2$C$\underline{H}_2$CH$_2$—) |
| 1.68 | (3H, d, —CH(C$\underline{H}_3$)N—) |
| 2.19 | (2H, t, —C$\underline{H}_2$COO—) |
| 4.07 | (2H, t, —OC$\underline{H}_2$CH$_2$CH$_2$CH$_2$—) |
| 5.12 | (1H, q, —C$\underline{H}$(CH$_3$)N—) |
| 6.80–7.20 | (7H, m, C$\underline{H}$ at 4 and 5 positions of imidazole ring + phenyl ring) |
| 7.42 | (1H, bs, —N=C$\underline{H}$—N—) | tert-butyl(±)(Z)-5-[1-phenyl-2-(imidazol-1-yl)-2-methylethylidene]aminoxypentanoate:

| NMR (CDCl$_3$): | |
|---|---|
| 1.44 | (9H, s, —(C$\underline{H}_3$)$_3$) |
| 1.60 | (4H, m, —OCH$_2$C$\underline{H}_2$C$\underline{H}_2$CH$_2$—) |
| 1.73 | (3H, d, —CH(C$\underline{H}_3$)N—) |
| 2.28 | (2H, t, —C$\underline{H}_2$COO—) |
| 4.23 | (2H, t, —OC$\underline{H}_2$CH$_2$CH$_2$CH$_2$—) |
| 5.97 | (1H, q, —C$\underline{H}$(CH$_3$)N—) |
| 6.80–7.20 | (7H, m, C$\underline{H}$ at 4 and 5 positions of imidazole ring + phenyl ring) |
| 7.52 | (1H, bs, —N=C$\underline{H}$—N—) | ethyl (E)-5-[1-cyclohexyl-2-(imidazol-1-yl)ethylidene]aminoxypentanoate:

| NMR (CDCl$_3$): | |
|---|---|
| 1–1.7 | (18H, m, protons of cyclohexyl ring + —CO—O—CH$_2$CH$_3$ + —O—CH$_2$—C$\underline{H}_2$—C$\underline{H}_2$—CH$_2$—) |
| 2.3 | (2H, m, —C$\underline{H}_2$—CO$_2$CH$_2$CH$_3$) |
| 4.1 | (4H, m, —O—C$\underline{H}_2$—CH$_2$—CH$_2$— + —CO—O—C$\underline{H}_2$—CH$_3$) |
| 4.58 | (2H, s, —C$\underline{H}_2$N=) |
| 6.9 | (1H, bs, C$\underline{H}$ at 5 position of imidazole ring) |
| 7.1 | (1H, bs, C$\underline{H}$ at 4 position of imidazole ring) |
| 7.6 | (1H, bs, —N=C$\underline{H}$—N) | ethyl (Z)-5-[1-cyclohexyl-2-(imidazol-1-yl)ethylidene]aminoxypentanoate:
Microanalysis: Found: C 63.25; H 8.74; N 12.17 Calculated for C$_{18}$H$_{29}$N$_3$O$_3$: C 64.45; H 8.71; N 12.53

| NMR (CDCl$_3$): | |
|---|---|
| 1.24 | (3H, t, —CO—O—CH$_2$—C$\underline{H}_3$) |
| 1.0–1.4 | (6H, m, C$\underline{H}_2$ at 3, 4, 5 positions of cyclohexyl ring) |
| 1.5–1.8 | (8H, m, C$\underline{H}_2$ at 2, 6 positions of cyclohexyl ring + —O—CH$_2$—C$\underline{H}_2$—C$\underline{H}_2$—CH$_2$—) |
| 2.0 | (1H, m, C$\underline{H}$ at 1 position of cyclohexyl ring) |
| 2.32 | (2H, m, —C$\underline{H}_2$—CO$_2$CH$_2$CH$_3$) |
| 4.12 | (4H, m, —O—C$\underline{H}_2$—CH$_2$—CH$_2$— + —CO—O—C$\underline{H}_2$CH$_3$) |
| 4.74 | (2H, s, —C$\underline{H}_2$—N=) |
| 6.90 | (1H, bs, C$\underline{H}$ at 5 position of imidazole ring) |
| 7.05 | (1H, bs, C$\underline{H}$ at 4 position of imidazole ring) |
| 7.54 | (1H, bs, —N=C$\underline{H}$—N—) |
| MS | 335 $\overline{M}]^+$. | tert-butyl (E)-5-[1-cyclohexyl-2-(imidazol-1-yl)-ethylidene]aminoxypentanoate:

| NMR (CDCl$_3$): | |
|---|---|
| 1.15 | (6H, m, —C$\underline{H}_2$ at 3, 4, 5 positions of cyclohexyl) |
| 1.45 | (9H, s, —C(C$\underline{H}_3$)$_3$) |
| 1.7 | (9H, m, C$\underline{H}$ at 1 position of cyclohexyl ring + C$\underline{H}_2$ at 2, 6 positions of cyclohexyl ring + —O—CH$_2$—C$\underline{H}_2$—C$\underline{H}_2$—CH$_2$—) |
| 2.25 | (2H, m, —C$\underline{H}_2$—CO$_2$—C(CH$_3$)$_3$) |
| 4.05 | (2H, m, —O—C$\underline{H}_2$—CH$_2$—CH$_2$—) |
| 4.55 | (2H, s, —C$\underline{H}_2$—N=) |
| 6.9 | (1H, bs, C$\underline{H}$ at 5 position of imidazole ring) |
| 7.05 | (1H, bs, C$\underline{H}$ at 4 position of imidazole ring) |
| 7.5 | (1H, bs, —N=C$\underline{H}$—N) | tert-butyl (Z)-5-[1-cyclohexyl-2-(imidazol-1-yl)-ethylidene]aminoxypentanoate:

| NMR (CDCl$_3$): | |
|---|---|
| 1.2 | (6H, m, —C$\underline{H}_2$ at 3, 4, 5 positions of cyclohexyl ring) |
| 1.4 | (9H, s, —C(C$\underline{H}_3$)$_3$) |
| 1.7 | (9H, m, C$\underline{H}$ at 1 position of cyclohexyl ring + C$\underline{H}_2$ at 2, 6 positions of cyclohexyl ring + —O—CH$_2$—C$\underline{H}_2$—C$\underline{H}_2$—CH$_2$—) |
| 2.25 | (2H, m, —C$\underline{H}_2$—CO$_2$—C(CH$_3$)$_3$) |

-continued

NMR (CDCl$_3$):

| | |
|---|---|
| 4.1 | (2H, m, —O—C$\underline{H}_2$—CH$_2$—CH$_2$—) |
| 4.74 | (2H, s, —C$\underline{H}_2$—N=) |
| 6.9 | (1H, bs, C$\underline{H}$ at 5 position of imidazole ring) |
| 7.05 | (1H, bs, C$\underline{H}$ at 4 position of imidazole ring) |
| 7.5 | (1H, bs, —N=C$\underline{H}$—N) | ethyl (Z)-4-[1-cyclohexyl-2-(imidazol-1-yl)ethylidene]aminoxybutanoate:

NMR (CDCl$_3$):

| | |
|---|---|
| 1.24 | (3H, t, —CO—O—CH$_2$C$\underline{H}_3$) |
| 1.1–1.4 | (6H, m, C$\underline{H}_2$ at 3, 4, 5 positions of cyclohexyl ring) |
| 1.55–1.8 | (4H, m, C$\underline{H}_2$ at 2, 6 positions of cyclohexyl ring) |
| 1.95 | (1H, m, C$\underline{H}$ at 1 position of cyclohexyl ring) |
| 2.1 | (2H, m, —C$\underline{H}_2$—CH$_2$—CO—) |
| 2.4 | (2H, m, —CH$_2$—C$\underline{H}_2$—CO—) |
| 4.15 | (4H, m, —O—C$\underline{H}_2$—CH$_2$—CH$_2$— + —CO—O—C$\underline{H}_2$CH$_3$) |
| 4.75 | (2H, s, —C$\underline{H}_2$—N=) |
| 6.90 | (1H, bs, C$\underline{H}$ at 5 position of imidazole ring) |
| 7.05 | (1H, bs, C$\underline{H}$ at 4 position of imidazole ring) |
| 7.48 | (1H, bs, —N=C$\underline{H}$—N—) |

EXAMPLE 3

To a stirred solution of 3.8 g (0.0115 moles) of ethyl (Z)-5-[1-phenyl-2-(imidazol-1-yl)-ethylidene]aminoxypentanoate in 20 ml of ethanol, 35 ml of aqueous sodium hydroxyde 1N are added at room temperature. Stirring is continued for 2 hours, and ethanol is removed under vacuum without heating. The aqueous solution is acidified with acetic acid till pH 6 with external cooling. The precipitated product is filtered, washed with ether and filtered again, yielding 2.63 g (75%) of (Z)-5-[1-phenyl-2-(imidazol-1-yl)-ethylidene]aminoxypentanoic acid.
m.p. 89°–90° C.
Microanalysis: Found: C 63.14; H 6.35; N 13.74 Calculated for C$_{16}$H$_{19}$N$_3$O$_3$: C 63.77; H 6.35; N 13.94

NMR (DMSO):

| | |
|---|---|
| 1.4–1.8 | (4H, m, —OCH$_2$C$\underline{H}_2$C$\underline{H}_2$CH$_2$—) |
| 2.25 | (2H, m, —C$\underline{H}_2$COOH) |
| 4.23 | (2H, m, —OC$\underline{H}_2$CH$_2$CH$_2$CH$_2$—) |
| 5.30 | (2H, s, —C$\underline{H}_2$—N=) |
| 6.80 | (1H, bs, C$\underline{H}$ at 5 position of imidazole ring) |
| 7.00 | (1H, bs, C$\underline{H}$ at 4 position of imidazole ring) |
| 7.2–7.7 | (6H, m, —N=C$\underline{H}$—N— + phenyl ring) |

By the same procedures the following compounds can be prepared:

(Z)-4-[1-phenyl-2-(imidazol-1-yl)-ethylidene]aminoxybutanoic acid:
m.p. 108°–109° C.
Microanalysis: Found: C 62.23; H 5.98; N 14.42 Calculated for C$_{15}$H$_{17}$N$_3$O$_3$: C 62.71; H 5.96; N 14.62

NMR (CDCl$_3$):

| | |
|---|---|
| 2.11 | (2H, m, —OCH$_2$C$\underline{H}_2$CH$_2$—) |
| 2.41 | (2H, t, —C$\underline{H}_2$COOH) |
| 4.34 | (2H, t, —OC$\underline{H}_2$CH$_2$CH$_2$—) |
| 5.11 | (2H, s, —C$\underline{H}_2$—N=) |
| 6.83 | (1H, bs, C$\underline{H}$ at 5 position of imidazole ring) |
| 6.96 | (1H, bs, C$\underline{H}$ at 4 position of imidazole ring) |
| 7.30–7.55 | (5H, m, phenyl ring) |
| 7.65 | (1H, bs, —N=C$\underline{H}$—N—) |
| 10.50 | (1H, bs, —COO$\underline{H}$) |

(Z)-3-[1-phenyl-2-(imidazol-1-yl)ethylidene]aminoxymethylbenzoic acid
m.p. 140°–142° C.
Microanalysis: Found: C 66.51; H 5.10; N 12.00 Calculated for C$_{19}$H$_{17}$N$_3$O$_3$: C 68.04; H 5.10; N 12.52

NMR (DMSO):

| | |
|---|---|
| 5.38 | (4H, s, —C$\underline{H}_2$—N= + —OC$\underline{H}_2$—) |
| 6.78 | (1H, dd, C$\underline{H}$ at 5 position of imidazole ring) |
| 6.97 | (1H, dd, C$\underline{H}$ at 4 position of imidazole ring) |
| 7.25–8.10 | (10H, m, —N=C$\underline{H}$—N + phenyl rings) |

(Z)-5-[1-(3-trifluoromethylphenyl)-2-(imidazol-1-yl)-ethylidene]aminoxypentanoic acid:
m.p. 124°–6° C.
Microanalysis: Found: C 55.24; H 4.92; N 11.20 Calculated for C$_{17}$H$_{18}$F$_3$N$_3$O$_3$: C 55.28; H 4.91; N 11.38

NMR (CDCl$_3$):

| | |
|---|---|
| 1.6–1.9 | (4H, m, —OCH$_2$C$\underline{H}_2$C$\underline{H}_2$CH$_2$—) |
| 2.37 | (2H, m, —C$\underline{H}_2$COO—) |
| 4.32 | (2H, m, —OC$\underline{H}_2$CH$_2$CH$_2$CH$_2$—) |
| 6.87 | (1H, s, C$\underline{H}$ at 5 position of imidazole ring) |
| 7.02 | (1H, s, C$\underline{H}$ at 4 position of imidazole ring) |
| 7.40–7.75 | (4H, m, phenyl ring) |
| 7.86 | (1H, s, —N=C$\underline{H}$—N—) |

(Z)-5-[1-cyclohexyl-2-(imidazol-1-yl)ethylidene]aminoxypentanoic acid:
m.p. 80°–82° C.
Microanalysis: Found: C 62.26; H 7.85; N 13.46 Calculated for C$_{16}$H$_{25}$N$_3$O$_3$: C 62.5; H 8.2; N 13.67

NMR (CDCl$_3$):

| | |
|---|---|
| 1.0–1.4 | (6H, m, C$\underline{H}_2$ of 3, 4, 5 positions of cyclohexyl ring) |
| 1.55–1.85 | (8H, m, C$\underline{H}_2$ of 2, 6 positions of cyclohexyl ring + —O—CH$_2$—C$\underline{H}_2$—C$\underline{H}_2$—CH$_2$—) |
| 2.05 | (1H, m, C$\underline{H}$ at 1 position of cyclohexyl ring) |
| 2.35 | (2H, m, —C$\underline{H}_2$—COOH) |
| 4.10 | (2H, m, —O—C$\underline{H}_2$—CH$_2$—CH$_2$—) |
| 4.72 | (2H, s, —C$\underline{H}_2$—N=) |
| 6.91 | (1H, bs, C$\underline{H}$ at 5 position of imidazole ring) |
| 7.05 | (1H, bs, C$\underline{H}$ at 4 position of imidazole ring) |
| 7.66 | (1H, bs, —N=C$\underline{H}$—N—) |

(E)-5-[1-cyclohexyl-2-(imidazol-1-yl)e-
thylidene]aminoxypentanoic acid:
m.p. 117°–119° C.
Microanalysis: Found: 62.14; H 13.34; N 8.01 Calculated for $C_{16}H_{25}N_3O_3$: C 62.5; H 8.2; N 13.67

| NMR (CDCl₃): | |
|---|---|
| 1.0–1.4 | (6H, m, C$\underline{H}_2$ at 3, 4, 5 positions of cyclohexyl ring) |
| 1.5–1.8 | (8H, m, C$\underline{H}_2$ at 2, 6 positions of cyclohexyl ring + —O—CH$_2$—C$\underline{H}_2$—C$\underline{H}_2$—CH$_2$—) |
| 2.40 | (2H, m, —C$\underline{H}_2$—COOH) |
| 2.97 | (1H, m, C$\underline{H}$ at 1 position of cyclohexyl ring) |
| 4.08 | (2H, m, —O—C$\underline{H}_2$—CH$_2$—CH$_2$—) |
| 4.56 | (2H, s, —C$\underline{H}_2$—N=) |
| 6.94 | (1H, bs, C$\underline{H}$ at 5 position of imidazole ring) |
| 7.07 | (1H, bs, C$\underline{H}$ at 4 position of imidazole ring) |
| 7.68 | (1H, bs, —N=C$\underline{H}$—N—) |

(Z)-4-[1-cyclohexyl-2-(imidazol-1-yl)e-
thylidene]aminoxybutanoic acid:
m.p. 120°–122° C.
Microanalysis: Found: C 60.74; H 8.28; N 13.83 Calculated for: $C_{15}H_{23}N_3O_3$: C 61.41; H 7.90; N 14.3

| NMR (CDCl₃): | |
|---|---|
| 1.1–1.4 | (6H, m. C$\underline{H}_2$ at 3, 4, 5 positions of cyclohexyl ring) |
| 1.6–1.8 | (4H, m. C$\underline{H}_2$ at 2, 6 positions of cyclohexyl ring) |
| 1.95–2.15 | (3H. m, C$\underline{H}$ at 1 position of cyclohexyl ring + —O—CH$_2$—C$\underline{H}_2$—CH$_2$—) |
| 2.39 | (2H, t, —C$\underline{H}_2$—COOH) |
| 4.17 | (2H, t, —O—C$\underline{H}_2$—CH$_2$—CH$_2$—) |
| 4.65 | (2H, s, —C$\underline{H}_2$—N=) |
| 6.85 | (1H, bs, C$\underline{H}$ at 5 position of imidazole ring) |
| 7.02 | (1H, bs, C$\underline{H}$ at 4 position of imidazole ring) |
| 7.50 | (1H. bs, —N=C$\underline{H}$—N—) |

(Z)-6-[1-phenyl-2-(imidazol-1-yl)ethylidene]aminox-
yhexanoic acid:
m.p. 109°–110° C.
Microanalysis: Found: C 64.42; H 6.72; N 13.10 Calculated for $C_{17}H_{21}N_3O_3$: C 64.74; H 6.71; N 13.31

| NMR (DMSO): | |
|---|---|
| 1.3–1.8 | (6H, m, —O—CH$_2$—C$\underline{H}_2$—C$\underline{H}_2$—C$\underline{H}_2$—CH$_2$—) |
| 2.22 | (2H, t, —C$\underline{H}_2$—COO—) |
| 4.22 | (2H, t, —O—C$\underline{H}_2$—CH$_2$—CH$_2$—) |
| 5.30 | (2H, s, —C$\underline{H}_2$—N=) |
| 6.8–7.7 | (8H, m phenyl ring + imidazole ring) | and analogously:
(Z)-5-[1-(3-bromophenyl)-2-(imidazol-1-yl)e-
thylidene]aminoxypentanoic acid;
(Z)-4-[1-(3-trifluoromethylphenyl)-2-(imidazol-1-yl)e-
thylidene]aminoxybutanoic acid;
(Z)-5-[1-(3-(n-butyl)phenyl)-2-(imidazol-1-yl)e-
thylidene]aminoxypentanoic acid;
(Z)-5-[1-(2-methoxyphenyl)-2-(imidazol-1-yl)e-
thylidene]aminoxypentanoic acid;
(Z)-3-oxa-5-[1-phenyl-2-(imidazol-1-yl)e-
thylidene]aminoxypentanoic acid;
(Z)-3-oxa-5-[1-(3-trifluoromethylphenyl)-2-(imidazol-1-yl)ethylidene]aminoxypentanoic acid;
(Z)-5-[1-(3-n-butyloxyphenyl)-2-(imidazol-1-yl)e-
thylidene]aminoxypentanoic acid:
m.p. 104°–105° C.
Microanalysis: Found: C 64.28; H 7.28; N 11.10 Calculated for $C_{20}H_{27}N_3O_4$: C 64.32; H 7.24; N 11.25

| NMR (CDCl₃): | |
|---|---|
| 0.95 | (3H, t, C$\underline{H}_3$—CH$_2$—CH$_2$—) |
| 1.35–1.9 | (8H, m, CH$_3$—C$\underline{H}_2$—C$\underline{H}_2$—CH$_2$—O— + —O—CH$_2$—C$\underline{H}_2$—C$\underline{H}_2$—CH$_2$—COO—) |
| 2.35 | (2H, m, —C$\underline{H}_2$—COO—) |
| 3.93 | (2H, t, —O—C$\underline{H}_2$—CH$_2$—CH$_2$—CH$_3$) |
| 4.25 | (2H, m, —O—C$\underline{H}_2$—CH$_2$—CH$_2$—COO—) |
| 5.13 | (2H, s, —C$\underline{H}_2$—N=) |
| 6.75–7.7 | (2H, s, —C$\underline{H}_2$—N=) |

(Z)-5-[1-(3-pyridyl)-2-(imidazol-1-yl)e-
thylidene]aminoxypentanoic acid:
m.p. 65°–70° C.
Microanalysis: Found: C 58.90; H 6.01; N 17.93 Calculated for $C_{15}H_{18}N_4O_3$: C 59.59; H 6.00; N 18.53

| NMR (CDCl₃): | |
|---|---|
| 1.6–1.9 | (4H, m, —O—CH$_2$—C$\underline{H}_2$—C$\underline{H}_2$—CH$_2$—) |
| 2.35 | (2H, m, —C$\underline{H}_2$—COO—) |
| 4.30 | (2H, m, —OC$\underline{H}_2$—CH$_2$—CH$_2$—CH$_2$—) |
| 5.20 | (2H, s, —C$\underline{H}_2$—N=) |
| 6.85–7.90 | (5H, m, C$\underline{H}$ at 4 and 5 positions of pyridine ring + imidazole ring) |
| 8.58 | (1H, dd, C$\underline{H}$ at 6 position of pyridine ring) |
| 8.81 | (1H, d, C$\underline{H}$ at 2 position of pyridine ring) |

(Z)-4-[1-(3-pyridyl)-2-(imidazol-1-yl)e-
thylidene]aminoxybutanoic acid:
Microanalysis: Found: C 57.41; H 5.54; N 18.92 Calculated for $C_{14}H_{16}N_4O_3$: C 61.30; H 5.82; N 20.43

| NMR (CDCl₃): | |
|---|---|
| 2.11 | (2H, m, —O—CH$_2$—C$\underline{H}_2$—CH$_2$—COO—) |
| 2.43 | (2H, m, —C$\underline{H}_2$—COO—) |
| 4.37 | (2H, m, —O—C$\underline{H}_2$—CH$_2$—CH$_2$—) |
| 5.13 | (2H, s, —C$\underline{H}_2$—N=) |
| 6.8–7.8 | (5H, m, C$\underline{H}$ at 4 and 5 positions of pyridine ring + imidazole ring) |
| 8.55 | (1H, dd, C$\underline{H}$ at 6 position of pyridine ring) |
| 8.76 | (1H, d, C$\underline{H}$ at 2 position of pyridine ring) |

(E)-4-[1-cyclohexyl-2-(imidazol-1-yl)e-
thylidene]aminoxybutanoic acid:
m.p. 126°–129° C.
Microanalysis Found: C 61,22; H 7.73; N 13.93 Calculated for $C_{15}H_{23}N_3O_3$: C 61.41; H 7.90; N 14.3

| NMR (CDCl$_3$): | |
|---|---|
| 0.9–1.75 | (10H, m, C$\underline{H}_2$ at 2, 3, 4, 5, 6 position of cyclohexyl ring) |
| 2.0 | (2H, m, —O—CH$_2$—C$\underline{H}_2$—CH$_2$—) |
| 2.40 | (2H, m, —C$\underline{H}_2$—COOH) |
| 2.95 | (1H, m, C$\underline{H}$ at 1 position of cyclohexyl ring) |
| 4.10 | (2H, m, —O—C$\underline{H}_2$—CH$_2$—CH$_2$—) |
| 4.55 | (2H, s, —C$\underline{H}_2$—N=) |
| 6.93 | (1H, bs, C$\underline{H}$ at 5 postion of imidazole ring) |
| 7.06 | (1H, bs, C$\underline{H}$ at 4 position of imidazole ring) |
| 7.68 | (1H, bs, —N=C$\underline{H}$—N—) |

(Z)-6-[1-cyclohexyl-2-(imidazol-1-yl)ethylidene]aminoxyhexanoic acid:
m.p. 107°–108° C.

Microanalysis: Found: C 63.08; H 8.57; N 8.01 Calculated for C$_{17}$H$_{27}$N$_3$O$_3$: C 63.53; H 8.47; N 13.07

| NMR (CDCl$_3$): | |
|---|---|
| 1.1–1.85 | (16H, m, C$\underline{H}_2$ at 2, 3, 4, 5, 6 position of cyclohexyl ring + —O—CH$_2$—C$\underline{H}_2$—C$\underline{H}_2$—CH$_2$—) |
| 2.05 | (1H, m, C$\underline{H}$ at 1 position of cyclohexyl ring) |
| 2.33 | (2H, m, —C$\underline{H}_2$—COOH) |
| 4.07 | (2H, m, —O—C$\underline{H}_2$—CH$_2$—CH$_2$—) |
| 4.69 | (2H, s, —C$\underline{H}_2$—N=) |
| 6.88 | (1H, bs, C$\underline{H}$ at 5 postion of imidazole ring) |
| 7.02 | (1H, bs, C$\underline{H}$ at 4 position of imidazole ring) |
| 7.63 | (1H, bs, —N=C$\underline{H}$—N—) |

(E)-5-[1-n-hexyl-2-(imidazol-1-yl)ethylidene]aminoxypentanoic acid:
m.p. 82°–85° C.

Microanalysis: Found: C 61.81; H 8.54; N 13.28 Calculated for C$_{16}$H$_{27}$N$_3$O$_3$: C 62.11; H 8.79; N 13.58

| NMR (CDCl$_3$): | |
|---|---|
| 0.87 | (3H, m, C$\underline{H}_3$—CH$_2$—CH$_2$—) |
| 1.05–1.58 | (8H, m, CH$_3$—(C$\underline{H}_2$)$_4$—) |
| 1.58–1.94 | (4H, m, —O—CH$_2$—C$\underline{H}_2$—C$\underline{H}_2$—CH$_2$—) |
| 1.94–2.60 | (4H, m, —C$\underline{H}_2$—COO— + —CH$_2$—C$\underline{H}_2$—C=N—) |
| 4.11 | (2H, m, —O—C$\underline{H}_2$—CH$_2$—CH$_2$—CH$_2$) |
| 4.57 | (2H, s, —C$\underline{H}_2$—N=) |
| 6.94 | (1H, bs, C$\underline{H}$ at 5 postion of imidazole ring) |
| 7.09 | (1H, bs, C$\underline{H}$ at 4 position of imidazole ring) |
| 7.66 | (1H, bs, —N=C$\underline{H}$—N—) |

(Z)-5-[1-n-hexyl-2-(imidazol-1-yl)ethylidene]aminoxypentanoic acid:
Microanalysis: Found: C 61.94; H 8.79; N 13.36 Calculated for C$_{16}$H$_{27}$N$_3$O$_3$: C 62.11; H 8.79; N 13.58

| NMR (CDCl$_3$): | |
|---|---|
| 0.87 | (3H, m, C$\underline{H}_3$—CH$_2$—CH$_2$) |
| 1.02–1.60 | (8H, m, CH$_3$—(C$\underline{H}_2$)$_4$—) |
| 1.60–1.88 | (4H, m, —O—CH$_2$—C$\underline{H}_2$—C$\underline{H}_2$—CH$_2$—) |
| 1.88–2.24 | (2H, m, —CH$_2$—C$\underline{H}_2$—C=N—) |
| 2.39 | (2H, m, —C$\underline{H}_2$—COO—) |
| 4.14 | (2H, m, —O—C$\underline{H}_2$—CH$_2$—CH$_2$—CH$_2$—) |
| 4.81 | (2H, s, —C$\underline{H}_2$—N=) |
| 6.92 | (1H, bs, C$\underline{H}$ at 5 postion of imidazole ring) |
| 7.10 | (1H, bs, C$\underline{H}$ at 4 postion of imidazole ring) |
| 7.65 | (1H, bs, —N=C$\underline{H}$—N—) |

4-[1-phenyl-3-(imidazol-1-yl)propylidene]aminoxybutanoic acid;

3-oxa-5-[1-cyclohexyl-2-(imidazol-1-yl)ethylidene]aminoxypentanoic acid;

5-[1-(3,3-dimethylcyclohexyl)-2-(imidazol-1-yl)ethylidene]aminoxypentanoic acid;

5-[1-cyclopentyl-2-(imidazol-1-yl)ethylidene]aminoxypentanoic acid;

(Z)-5-[1-(2-thienyl)-2-(imidazol-1-yl)ethylidene]aminoxypentanoic acid;

3-oxa-6-[1-cyclohexyl-2-(imidazol-1-yl)ethylidene]aminoxyhexanoic acid;

5-[1-cycloheptyl-2-(imidazol-1-yl)ethylidene]aminoxypentanoic acid;

6-[1-cycloheptyl-2-(imidazol-1-yl)ethylidene]aminoxyhexanoic acid; and

5-[1-n-heptyl-2-(imidazol-1-yl)ethylidene]aminoxypentanoic acid.

EXAMPLE 4

Trifluoroacetic acid (1.3 ml) is added dropwise at −10° C. to 0.23 g (0.643 mmoles) of tert-butyl (E)-5-[1-phenyl-2-(imidazol-1-yl)ethylidene]aminoxypentanoate. The mixture is stirred at −10° C. for 1 hour and 30 minutes. A cooled saturated sodium hydrogencarbonate solution is added to the reaction mixture at 0° C. till pH=7 and the mixture is extracted with ethyl acetate. The aqueous phase is cooled, acidified with acetic acid and extracted twice with ethyl acetate. The organic phase is dried and evaporated. The residue is taken up twice with toluene and evaporated under vacuum without heating, yielding 0.11 g (57%) of (E)-5-[1-phenyl-2-(imidazol-1-yl)ethylidene]aminoxypentanoic acid.

Microanalysis: Found: C 59.12; H 5.93; N 12.23 Calculated for C$_{16}$H$_{19}$N$_3$O$_3$: C 63.77; H 6.35; N 13.94

| NMR (CDCl$_3$): | |
|---|---|
| 1.75 | (4H, m, —OCH$_2$C$\underline{H}_2$C$\underline{H}_2$CH$_2$—) |
| 2.39 | (2H, m, —C$\underline{H}_2$COOH) |
| 4.12 | (2H, m, —OC$\underline{H}_2$CH$_2$CH$_2$CH$_2$—) |
| 4.92 | (2H, s, —C$\underline{H}_2$—N=) |
| 6.87 | (1H, bs, C$\underline{H}$ at 5 postion of imidazole ring) |
| 7.02 | (1H, bs, C$\underline{H}$ at 4 position of imidazole ring) |
| 7.2–7.5 | (5H, m, phenyl ring) |

| NMR (CDCl₃): | |
|---|---|
| 7.72 | (1H, bs, —N=C$\underline{H}$—N—) |

By the same procedure the following compounds can be prepared:

(±)(E)-5-[1-phenyl-2-(imidazol-1-yl)-2-methylethylidene]aminoxypentanoic acid:

Microanalysis: Found: C 64.20; H 6.56; N 12.72 Calculated for C₁₇H₂₁N₃O₃: C 64.74; H 6.71; N 13.32

| NMR (CDCl₃): | |
|---|---|
| 1.5–1.8 | (7H, m, —CH(C$\underline{H}$₃)N— + —OCH₂C$\underline{H}$₂C$\underline{H}$₂CH₂) |
| 2.35 | (2H, m, —C$\underline{H}$₂COO—) |
| 4.10 | (2H, m, —OC$\underline{H}$₂CH₂CH₂CH₂—) |
| 5.24 | (1H, q, —C$\underline{H}$(CH₃)N—) |
| 6.9–7.5 | (7H, m, C$\underline{H}$ at 4 and 5 positions of imidazole ring + phenyl ring) |
| 8.01 | (1H, bs, —N=C$\underline{H}$—N—) |

(±) (Z)-5-[1-phenyl-2-(imidazol-1-yl)-2-methylethylidene]aminoxypentanoic acid;

| NMR (CDCl₃): | |
|---|---|
| 1.6–1.9 | (7H, m, —CH(C$\underline{H}$₃)N— + —OCH₂C$\underline{H}$₂C$\underline{H}$₂CH₂—) |
| 2.40 | (2H, m, —C$\underline{H}$₂COO—) |
| 4.25 | (2H, m, —OC$\underline{H}$₂CH₂CH₂CH₂—) |
| 5.98 | (1H, q, —C$\underline{H}$(CH₃)N—) |
| 6.8–7.4 | (7H, m, C$\underline{H}$ at 4 and 5 positions of imidazole ring + phenyl ring) |
| 7.82 | (1H, bs, —N=C$\underline{H}$—N—) | and analogously:

(E)-4-[1-phenyl-2-(imidazol-1-yl)ethylidene]aminoxybutanoic acid;

(E)-5-[1-(3-trifluoromethylphenyl)-2-(imidazol-1-yl)ethylidene]aminoxypentanoic acid;

(E)-5-[1-(3-bromophenyl)-2-(imidazol-1-yl)ethylidene]aminoxypentanoic acid;

(E)-4-[1-(3-trifluoromethylphenyl)-2-(imidazol-1-yl)ethylidene]aminoxybutanoic acid;

(E)-5-[1-(3-(n-butyl)phenyl)-2-(imidazol-1-yl)ethylidene]aminoxypentanoic acid;

(E)-5-[1-(2-methoxyphenyl)-2-(imidazol-1-yl)ethylidene]aminoxypentanoic acid;

(E)-3-oxa-5-[1-phenyl-2-(imidazol-1-yl)ethylidene]aminoxypentanoic acid;

(E)-3-oxa-5-[1-(3-trifluoromethylphenyl)-2-(imidazol-1-yl)ethylidene]aminoxypentanoic acid;

(E)-3-[1-phenyl-2-(imidazol-1-yl)ethylidene]aminoxymethylbenzoic acid;

(E)-5-[1-(2-thienyl)-2-(imidazol-1-yl)ethylidene]aminoxypentanoic acid;

(E)-5-[1-(3-pyridyl)-2-(imidazol-1-yl)ethylidene]aminoxypentanoic acid; and (E)-4-[1-(3-pyridyl)-2-(imidazol-1-yl)ethylidene]aminoxybutanoic acid.

EXAMPLE 5

To a stirred mixture of 0.50 g (0.0025 moles) of (Z)-1-phenyl-2-(imidazol-1-yl)ethanone oxime and 2 ml of dimethylformamide, 0.15 g (0.0034 moles) of sodium hydride dispersion 55% are added portionwise at room temperature. Upon completion, stirring is continued till hydrogen evolution stops; then 0.42 g (0.0049 moles) of γ-butyrolactone are added and the mixture is heated at 80° C. for 4 hours.

The reaction mixture is evaporated under vacuum, diluted with water and acidified with acetic acid till pH 6, with external cooling. The precipitated product is filtered, washed with ether and filtered again, yielding 0.40 g (56%) of (Z)-4-[1-phenyl-2-(imidazol-1-yl)ethylidene]aminoxybutanoic acid.

m.p. 108°–109° C.

Microanalysis: Found: C 62.23; H 5.98; N 14.42 Calculated for C₁₅H₁₇N₃O₃: C 62.71; H 5.96; N 14.62

| NMR (CDCl₃): | |
|---|---|
| 2.11 | (2H, m, —CH₂C$\underline{H}$₂CH₂—) |
| 2.41 | (2H, t, —C$\underline{H}$₂COOH) |
| 4.34 | (2H, t, —OC$\underline{H}$₂CH₂CH₂—) |
| 5.11 | (2H, s, —C$\underline{H}$₂—N=) |
| 6.83 | (1H, bs, C$\underline{H}$ at 5 position of imidazole ring) |
| 6.96 | (1H, bs, C$\underline{H}$ at 4 position of imidazole ring) |
| 7.30–7.55 | (5H, m, phenyl ring) |
| 7.65 | (1H, bs, —N=C$\underline{H}$—N—) |
| 10.50 | (1H, bs, —COOH) |

By proceeding analogously the following compounds can be obtained:

4-[1-(3-trifluoromethylphenyl)-2-(imidazol-1-yl)ethylidene]aminoxybutanoic acid:

4-[1-phenyl-3-(imidazol-1-yl)propylidene]aminoxybutanoic acid:

4-[1-cyclohexyl-2-(imidazol-1-yl)ethylidene]aminoxybutanoic acid: and

4-[1-(3-pyridyl)-2-(imidazol-1-yl)ethylidene]aminoxybutanoic acid.

EXAMPLE 6

To a solution of 400 mg (1.19 mmoles) of ethyl (E)-5-[1-cyclohexyl-2-(imidazol-1-yl)ethylidene] aminoxypentanoate in 5 ml of 1,4-dioxane, 9 ml of an aqueous ammonium hydroxide solution 30% are added. After stirring for 48 hours at room temperature the reaction mixture is diluted with water, extracted twice with ethyl acetate, dried and evaporated. The residue is purified by column chromatography over silica gel (eluant: methylene chloride/methanol=95/5). The pure fractions are collected and evaporated, yielding 140 mg (60%) of (E)-5-[1-cyclohexyl-2-(imidazol-1-yl)ethylidene]aminoxypentanamide.

| NMR (CDCl₃): | |
|---|---|
| 1.0–1.4 | (6H, m, C$\underline{H}$₂ at 3, 4, 5 positions of cyclohexyl ring) |
| 1.5–1.8 | (8H, m, C$\underline{H}$₂ at 2, 6 positions of cyclohexyl ring + —O—CH₂—C$\underline{H}$₂—C$\underline{H}$₂—CH₂—) |
| 2.25 | (2H, m, —C$\underline{H}$₂CO—) |
| 2.93 | (1H, m, C$\underline{H}$ at 1 position of cyclohexyl ring) |
| 4.07 | (2H, m, —O—C$\underline{H}$₂—CH₂—CH₂—) |

-continued

NMR (CDCl$_3$):

| | |
|---|---|
| 4.57 | (2H, s, —C$\underline{H}_2$—N=) |
| 4.70 | (1H, bs. CON$\underline{H}$) |
| 5.70 | (1H, bs. CON$\underline{H}$) |
| 6.93 | (1H, bs, C$\underline{H}$ at 5 position of imidazole ring) |
| 7.06 | (1H, bs, C$\underline{H}$ at 4 position of imidazole ring) |
| 7.63 | (1H, bs. —N=C$\underline{H}$—N—) |

By proceeding analogously the following compound can be prepared:
(Z)-5-1[1-(3-pyridyl)-2-(imidazol-1-yl)e-thylidene]aminoxypentanamide:
m.p. 102°–107° C.

Microanalysis: Found: C 58.69; H 6.35; N 21.93 Calculated for C$_{15}$H$_{19}$N$_5$O$_2$: C 59.80; H 6.36; N 23.24

NMR (CDCl$_3$):

| | |
|---|---|
| 1.6–1.9 | (4H, m, —O—CH$_2$—C$\underline{H}_2$—C$\underline{H}_2$—CH$_2$—) |
| 2.20 | (2H, m, —C$\underline{H}_2$—CONH$_2$) |
| 4.3 | (2H, m, —O—C$\underline{H}_2$—CH$_2$—CH$_2$—CH$_2$) |
| 5.17 | (2H, s, —C$\underline{H}_2$—N=) |
| 5.55 | (1H, bs, —CO—$\underline{N}H_A$) |
| 5.90 | (1H, bs. —CO—$\underline{N}H_B$) |
| 6.8–7.9 | (5H, m. C$\underline{H}$ at 4 and 5 positions of pyridine ring + imidazole ring) |
| 8.59 | (1H, dd, C$\underline{H}$ at 6 position of pyridine ring) |
| 8.82 | (1H, d. C$\underline{H}$ at 2 position of pyridine ring) | and similarly:
5-[1-phenyl-2-(imidazol-1-yl)ethylidene]aminoxypentanamide.

EXAMPLE 7

To a stirred mixture of 1.5 g (0.005 moles) of (±)(E+Z)-1-phenyl-2-(imidazol-1-yl)-2-benzyletha-none oxime and 10 ml of dimethylformamide, 0.26 g (0.006 moles) of sodium hydride dispersion 55% are added portionwise at room temperature. Upon completion, stirring is continued till hydrogen evolution stops. Then 0.79 ml (0.005 moles) of ethyl 5-bromopentanoate are added at room temperature and stirring is continued for 6 hours. The reaction mixture is diluted with water and extracted twice with ethyl acetate. The organic phase is washed with water and with saturated sodium chloride solution, dried over anhydrous Na$_2$SO$_4$ and evaporated to dryness. The residue is purified by column chromatography over silica gel (eluant: dichloromethane/methanol=190/10) yielding 1.25 g (60%) of ethyl (±)(E+Z)-5-[1-phenyl-2-(imidazol-1-yl)-2-benzylethylidene]aminoxypentanoate.

Microanalysis: Found: C 70.31; H 6.92; N 9.54. Calculated for C$_{25}$H$_{29}$N$_3$O$_3$: C 71.58; H 6.97; N 10.02.

NMR (CDCl$_3$):

| | |
|---|---|
| 5.07 | (1H, dd, C$\underline{H}$—C=N—O, E isomer) |
| 6.03 | (1H, t, C$\underline{H}$—C=N—O, Z isomer) |

Analogously the following compound can be prepared:
ethyl (±)(E+Z)-5-[1-cyclohexyl-2-(imidazol-1-yl)-2-benzylethylidene]aminoxypentanoate.

EXAMPLE 8

To a stirred solution of 1 g (0.0024 moles) of ethyl (±)(E+Z)-5-[1-phenyl-2-(imidazol)-1-yl)-2-benzyle-thylidene]aminoxypentanoate in 20 ml of ethanol, 10 ml of aqueous sodium hydroxide 1N are added at room temperature. Stirring is continued for 30′ at 60° C. and then ethanol is removed under vacuum. The aqueous solution is acidified with acetic acid till pH 6 with external cooling and extracted three times with ethyl acetate. The organic phase is washed with water, with saturated sodium chloride solution, dried over anhydrous Na$_2$SO$_4$ and evaporated to dryness. The residue is purified by column chromatography over silica gel (eluant: chloroform/methanol=180/20) yielding 0.235 g of (±)(E)-5-[1-phenyl-2-(imidazol-1-yl)-2-benzyle-thylidene]aminoxypentanoic acid and 0.427 g of the corresponding "Z" isomer. (±)(E)-5-[1-phenyl-2-(imidazol-1-yl)-2-benzylethylidene]aminoxypentanoic acid:

Microanalysis: Found: C 69.13; H 6.58; N 10.33. Calculated for C$_{23}$H$_{25}$N$_3$O$_3$: C 70.57; H 6.44; N 10.73.

NMR (CDCl$_3$):

| | |
|---|---|
| 1.7 | (4H, m. —O—CH$_2$—C$\underline{H}_2$—C$\underline{H}_2$—CH$_2$—COO—) |
| 2.35 | (2H, m, —C$\underline{H}_2$—COO—) |
| 3.25 | (1H, dd, Ph—C$\underline{H}_A$—) |
| 3.49 | (1H, dd, Ph—C$\underline{H}_B$—) |
| 4.15 | (2H, m, —O—C$\underline{H}_2$—CH$_2$—CH$_2$—CH$_2$—COO—) |
| 5.09 | (1H, dd. —C$\underline{H}$—C=N—O) |
| 6.8–7.5 | (13H, m. 2 phenyl rings + imidazole ring) |

(±)(Z)-5-[1-phenyl-2-(imidazol-1-yl)-2-benzyle-thylidene]aminoxypentanoic acid:

Microanalysis: Found: C 68.21; H 6.68; N 9.94. Calculated for C$_{23}$H$_{25}$N$_3$O$_3$: C 70.57; H 6.44; N 10.73.

NMR (CDCl$_3$):

| | |
|---|---|
| 1.7 | (4H, m, —O—CH$_2$—C$\underline{H}_2$—C$\underline{H}_2$—CH$_2$—COO—) |
| 2.35 | (2H, m, —C$\underline{H}_2$—COO—) |
| 3.35 | (1H, dd, Ph—C$\underline{H}_A$—) |
| 3.49 | (1H, dd, Ph—C$\underline{H}_B$—) |
| 4.2 | (2H, m, —O—C$\underline{H}_2$—CH$_2$—CH$_2$—CH$_2$—COO—) |
| 6.00 | (1H, dd, —C$\underline{H}$—C=N—O) |
| 6.8–7.7 | (13H, m, 2 phenyl rings + imidazole ring) |

By the same procedure, starting from either an (E) or (Z) ester, prepared according to the method described in Example 1, or a mixture thereof, the following compounds can be prepared:
(±)(Z)-5-[1-cyclohexyl-2-(imidazol-1-yl)-2-benzyle-thylidene]aminoxypentanoic acid:

NMR (CDCl$_3$):

| | |
|---|---|
| 0.53–2.15 | (14H, m, —OCH$_2$—C$\underline{H}_2$CH$_2$CH$_2$—COO— + C$\underline{H}_2$ at 2, 3, 4, 5 and 6 positions of cyclohexyl ring) |
| 2.15–2.60 | (3H, m, —C$\underline{H}_2$COO— + C$\underline{H}$ at 1 position of cyclohexyl ring) |
| 2.76–3.60 | (2H, m, Ph—C$\underline{H}_2$—) |

-continued

| NMR (CDCl$_3$): | |
|---|---|
| 4.10 | (2H, m, —O—C$\underline{H}_2$—CH$_2$) |
| 5.62 | (1H, dd, —C$\underline{H}$—C=N—O) |
| 6.67-7.42 | (7H, m, phenyl ring + C$\underline{H}$ at 4 and 5 positions of imidazole ring) |
| 7.73 | (1H, bs, —N=C$\underline{H}$—N—); |

(±)(E)-5-[1-cyclohexyl-2-(imidazol-1-yl)-2-benzylethylidene]aminoxypentanoic acid:

| NMR (CDCl$_3$): | |
|---|---|
| 0.37-2.16 | (14H, m, —OCH$_2$C$\underline{H}_2$C$\underline{H}_2$—CH$_2$—COO— + C$\underline{H}_2$ at 2, 3, 4, 5 and 6 positions of cyclohexyl ring) |
| 2.41 | (2H, m, —C$\underline{H}$—COO—) |
| 2.61-3.63 | (3H, m, Ph—C$\underline{H}_2$ + C$\underline{H}$ at 1 position of cyclohexyl ring) |
| 4.19 | (2H, m, —O—C$\underline{H}_2$—CH$_2$—) |
| 4.87 | (1H, dd, —C$\underline{H}$—C=N—O) |
| 6.52-7.40 | (7H, m, phenyl ring + C$\underline{H}$ at 4 and 5 positions of imidazole ring) |
| 7.58 | (1H, bs, —N=C$\underline{H}$—N—); |

(±)(Z)-6-[1-phenyl-2-(imidazol-1-yl)-2-benzylethylidene]aminoxyhexanoic acid:

Microanalysis: Found: C 70.11; H 6.83; N 9.99. Calculated for C$_{24}$H$_{27}$N$_3$O$_3$: C 71.09; H 6.71; N 10.36.

| NMR (CDCl$_3$): | |
|---|---|
| 1.3-1.7 | (6H, m, —O—CH$_2$—C$\underline{H}_2$—C$\underline{H}_2$—C$\underline{H}_2$—CH$_2$—) |
| 2.35 | (2H, m, —C$\underline{H}_2$—COO—) |
| 3.33 | (1H, dd, Ph—C$\underline{H}_A$—) |
| 3.49 | (1H, dd, Ph—C$\underline{H}_B$—) |
| 4.2 | (2H, m, —OC$\underline{H}_2$CH$_2$CH$_2$CH$_2$CH$_2$—) |
| 5.97 | (1H, t, —C$\underline{H}$—C=N—O) |
| 6.8-7.8 | (13H, m, 2 phenyl rings + imidazole ring); |

(±)(E)-6-[1-phenyl-2-(imidazol-1-yl)-2-benzylethylidene]aminoxyhexanoic acid:

Microanalysis: Found: C 70.32; H 6.63; N 10.15 Calculated for C$_{24}$H$_{27}$N$_3$O$_3$: C 71.09; H 6.71; N 10.36

| NMR (CDCl$_3$): | |
|---|---|
| 1.2-1.8 | (6H, m, —OCH$_2$—C$\underline{H}_2$C$\underline{H}_2$—C$\underline{H}_2$—CH$_2$—) |
| 2.3 | (2H, m, —CH$_2$COO—) |
| 3.27 | (1H, dd, Ph—C$\underline{H}_A$—) |
| 3.51 | (1H, dd, Ph—C$\underline{H}_B$—) |
| 4.1 | (2H, m, —OC$\underline{H}_2$CH$_2$CH$_2$CH$_2$CH$_2$—) |
| 5.10 | (1H, dd, —C$\underline{H}$—C=N—O) |
| 6.8-7.6 | (13H, m, 2 phenyl rings + imidazole ring); |

(±)(Z)-6-[1-cyclohexyl-2-(imidazol-1-yl)-2-benzylethylidene]aminoxyhexanoic acid;
(±)(E)-6-[1-cyclohexyl-2-(imidazol-1-yl)-2-benzylethylidene]aminoxyhexanoic acid;
(±)(Z)-5-[1-(4-fluorophenyl)-2-(imidazol-1-yl)-2-(4-fluorobenzyl)ethylidene]aminoxypentanoic acid;
(±)(E)-5-[1-(4-fluorophenyl)-2-(imidazol-1-yl)-2-(4-fluorobenzyl)ethylidene]aminoxypentanoic acid;
(±)(Z)-5-[1-cyclohexyl-2-(imidazol-1-yl)-2-(4-fluorobenzyl)ethylidene]aminoxypentanoic acid;
(±)(E)-5-[1-cyclohexyl-2-(imidazol-1-yl)-2-(4-fluorobenzyl)ethylidene]aminoxypentanoic acid;
(±)(Z)-3-oxa-5-[1-phenyl-2-(imidazol-1-yl)-2-benzylethylidene]aminoxypentanoic acid; and
(±)(E)-3-oxa-5-[1-phenyl-2-(imidazol-1-yl)-2-benzylethylidene]aminoxypentanoic acid.

EXAMPLE 9

To a stirred solution of 1 g (0.005 moles) of (Z)-5-[1-phenyl-2-(imidazol)-1-yl)ethylidene]aminoxypentanoic acid in 10 ml of methanol, 820 mg (0.015 moles) of a sodium methoxide solution in methanol are added. The reaction mixture is evaporated and the precipitate product is filtered off and dried yielding 970 mg (60%) of sodium (Z)-5-[1-phenyl-2-(imidazol-1-yl)ethylidene]aminoxypentanoate.

EXAMPLE 10

Tablets, each weighing 150 mg and containing 50 mg of the active substance can be manufactured as follows:

| Composition (for 10,000 tablets) | |
|---|---|
| (Z)-5-[1-cyclohexyl-2-(imidazol-1-yl)ethylidene]aminoxypentanoic acid | 500 g |
| Lactose | 710 g |
| Corn starch | 237.5 g |
| Talc powder | 37.5 g |
| Magnesium stearate | 15 g |

(Z)-5-[1-cyclohexyl-2-(imidazol-1-yl)ethylidene]aminoxypentanoic acid, lactose and a half of the corn starch are mixed: the mixture is then forced through a sieve of 0.5 mm openings. Corn starch (18 mg) is suspended in warm water (180 ml). The resulting paste is used to granulate the powder. The granules are dried, comminuted on a sieve of sieve size 1.4 nm, then the remaining quantity of starch, talc and magnesium are added, carefully mixed, and processed into tablets using punches of 8 mm diameter.

EXAMPLE 11

Tablets, each weighing 150 mg and containing 50 mg of the active substance can be manufactured as follows:

| Composition (for 10,000 tablets) | |
|---|---|
| ±5-(E)-[1-phenyl-2-(imidazol-1-yl)-2-benzylethylidene]aminoxypentanoic acid | 500 g |
| Lactose | 710 g |
| Corn starch | 237.5 g |
| Talc powder | 37.5 g |
| Magnesium stearate | 15 g |

±5-(E)-[1-phenyl-2-(imidazol-1-yl)-2-benzylethylidene]aminoxypentanoic acid, lactose and a half of the corn starch are mixed: the mixture is then forced through a sieve of 0.5 mm openings. Corn starch (18 mg) is suspended in warm water (180 ml). The resulting paste is used to granulate the powder. The granules are dried, comminuted on a sieve of sieve size 1.4 mm, then the remaining quantity of starch, talc and magnesium are added, carefully mixed, and processed into tablets using punches of 8 mm diameter.

We claim:
1. A compound of the formula (I)

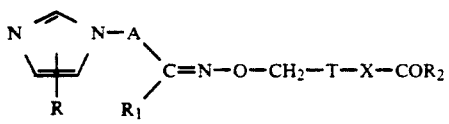 (I)

wherein
R is hydrogen or $C_1$–$C_4$ alkyl;
A is a $C_1$–$C_4$ alkylene chain unsubstituted or substituted by a phenyl ring unsubstituted or substituted by one or two substituents chosen independently from halogen and trifluoromethyl;
$R_1$ is a) hydrogen or a straight or branched, saturated or unsaturated $C_1$–$C_{10}$ hydrocarbon radical; b) an aryl or aryl-$C_1$–$C_4$ alkyl group, wherein the aryl group or the aryl moiety is selected from the group consisting of phenyl, naphthyl, thienyl and pyridyl groups and is unsubstituted or substituted either by one to four substituents independently chosen from halogen, trihalomethyl, $C_1$–$C_4$ alkyl, $C_2$–$C_3$ alkenyl, $C_2$–$C_6$ alkynyl, $C_1$–$C_4$ alkoxy, $C_1$–$C_4$ alkylthio and $C_1$–$C_4$ alkylsulfonyl or by a substituent chosen from $C_5$–$C_8$ alkyl, $C_4$–$C_8$ alkenyl, $C_5$–$C_8$ alkoxy, $C_5$–$C_8$ alkylthio and phenyl, in which the phenyl ring is unsubstituted or substituted by a substituent chosen from halogen, trihalomethyl and $C_1$–$C_4$ alkyl; or (c) a $C_5$–$C_8$ cycloalkyl or $C_5$–$C_8$ cycloalkyl-$C_1$–$C_4$ alkyl group, wherein the cycloalkyl group or moiety is unsubstituted or substituted by one to three $C_1$–$C_4$ alkyl groups;
T is a straight or branched, saturated or unsaturated $C_1$–$C_6$ hydrocarbon chain, or a phenylene radical;
X is a bond or a divalent group consisting of —O—$CH_2$—, —C(R'R'')—, —Si(R'R'')—, vinylene or isopropenylene, wherein each of R' and R'' being the same or different is hydrogen, fluorine or $C_1$–$C_4$ alkyl; $R_2$ is an —$OR_3$ or —$N(R_3R_4)$ group, wherein each of $R_3$ and $R_4$ independently is hydrogen, $C_1$–$C_6$ alkyl, phenyl or benzyl; or a pharmaceutically acceptable salt thereof.

2. A compound of formula (I), according to claim 1 wherein
R is hydrogen or methyl;
A is a $C_1$–$C_4$ alkylene chain unsubstituted or substituted by phenyl, in its turn unsubstituted or substituted by one or two substituents independently chosen from halogen and trifluoromethyl;
$R_1$ is a) $C_1$–$C_8$ alkyl or $C_2$–$C_8$ alkenyl; b) a phenyl, naphthyl, thienyl or pyridyl group unsubstituted or substituted either by one or two substituents independently chosen from halogen, trihalomethyl, $C_1$–$C_4$ alkyl, $C_1$–$C_4$ alkoxy, $C_1$–$C_4$ alkylsulfonyl and $C_1$–$C_4$ alkylthio, or by a substituent chosen from $C_5$–$C_8$ alkyl, $C_4$–$C_8$ alkenyl, $C_5$–$C_8$ alkoxy, $C_5$–$C_8$ alkylthio and phenyl, in which the phenyl ring is unsubstituted or substituted by a substituent chosen from halogen, trihalomethyl and $C_1$–$C_4$ alkyl; or (c) a cyclohexyl or cycloheptyl group unsubstituted or substituted by one or two $C_1$–$C_4$ alkyl groups;
T is a $C_1$–$C_5$ alkylene or $C_2$–$C_5$ alkenylene group; or a phenylene group;
X is a bond or a —O—$CH_2$— group;
$R_2$ is an —$OR_3$ or —$NHR_3$ group, wherein $R_3$ is hydrogen or $C_1$–$C_4$ alkyl; or a pharmaceutically acceptable salt thereof.

3. A compound of formula (I), according to claim 1, wherein
R is hydrogen;
A is —$CH_2$—, —$CH(CH_3)$—, —$CH_2$—$CH_2$— or —$CH(CH_2Ph)$— in which Ph means phenyl optionally substituted by a halogen atom;
$R_1$ is a) $C_5$–$C_7$ alkyl; b) a phenyl, pyridyl or thienyl ring, unsubstituted or substituted by halogen, $C_1$–$C_4$ alkyl, $C_1$–$C_4$ alkoxy or trifluoromethyl; or c) a cyclohexyl or cycloheptyl ring;
T is a $C_2$–$C_4$ alkylene or phenylene group;
X is a bond or a —O—$CH_2$— group;
$R_2$ is an —$OR_3$ group wherein $R_3$ is hydrogen or $C_1$–$C_4$ alkyl; or a pharmaceutically acceptable salt thereof.

4. A compound selected from the group consisting of the following, either as Z- or E-isomers or Z,E-mixtures of said isomers:
5-[1-phenyl-2-(imidazol-1-yl)ethylidene]aminoxypentanoic acid;
5-[1-phenyl-2-(imidazol-1-yl)ethylidene]aminoxypentanamide;
ethyl 4-[1-phenyl-2-(imidazol-1-yl)ethylidene]aminoxybutanoate;
4-[1-phenyl-2-(imidazol-1-yl)ethylidene]aminoxybutanoic acid;
methyl 3-[1-phenyl-2-(imidazol-1-yl)ethylidene]aminoxypropanoate;
ethyl 5-[1-(3-trifluoromethylphenyl)-2-(imidazol-1-yl)ethylidene]aminoxypentanoate;
5-[1-(3-trifluoromethylphenyl)-2-(imidazol-1-yl)ethylidene]aminoxypentanoic acid;
5-[1-(3-bromophenyl)-2-(imidazol-1-yl)ethylidene]aminoxypentanoic acid;
4-[1-(3-trifluoromethylphenyl)-2-(imidazol-1-yl)ethylidene]aminoxybutanoic acid;
5-[1-(3-(n-butyl)phenyl)-2-(imidazol-1-yl)ethylidene]aminoxypentanoic acid;
5-[1-(2-methoxyphenyl)-2-(imidazol-1-yl)ethylidene]aminoxypentanoic acid;
ethyl 3-oxa-5-[1-phenyl-2-(imidazol-1-yl)ethylidene]aminoxypentanoate;
3-oxa-5-[1-phenyl-2-(imidazol-1-yl)ethylidene]aminoxypentanoic acid;
3-oxa-5-[1-(3-trifluoromethylphenyl)-2-(imidazol-1-yl)ethylidene]aminoxypentanoic acid;
tert-butyl 5-[1-phenyl-2-(imidazol-1-yl)-2-methylethylidene]aminoxypentanoate;
5-[1-phenyl-2-(imidazol-1-yl)-2-methylethylidene]aminoxypentanoic acid;
3-[1-phenyl-2-(imidazol-1-yl)ethylidene]aminoxymethylbenzoic acid;
4-[1-phenyl-3-(imidazol-1-yl)propylidene]aminoxybutanoic acid;
5-[1-(n-hexyl)-2-(imidazol-1-yl)ethylidene]aminoxypentanoic acid;
ethyl 5-[1-cyclohexyl-2-(imidazol-1-yl)ethylidene]aminoxypentanoate;
tert-butyl 5-[1-cyclohexyl-2-(imidazol-1-yl)ethylidene]aminoxypentanoate;
5-[1-cyclohexyl-2-(imidazol-1-yl)ethylidene]aminoxypentanoic acid;
ethyl 4-[1-cyclohexyl-2-(imidazol-1-yl)ethylidene]aminoxybutanoate;
4-[1-cyclohexyl-2-(imidazol-1-yl)ethylidene]aminoxybutanoic acid;
5-[1-cyclohexyl-2-(imidazol-1-yl)ethylidene]aminoxypentanamide;

3-oxa-5-[1-cyclohexyl-2-(imidazol-1-yl)e-
thylidene]aminoxypentanoic acid;

5-[1-(3,3-dimethylcyclohexyl)-2-(imidazol-1-yl)e-
thylidene]aminoxypentanoic acid;

5-[1-cyclopentyl-2-(imidazol-1-yl)ethylidene]aminox-
ypentanoic acid;

5-[1-(2-thienyl)-2-(imidazol-1-yl)ethylidene]aminox-
ypentanoic acid;

ethyl 5-[1-(3-pyridyl)-2-(imidazol-1-yl)e-
thylidene]aminoxypentanoate;

5-[1-(3-pyridyl)-2-(imidazol-1-yl)ethylidene]aminox-
ypentanoic acid;

4-[1-(3-pyridyl)-2-(imidazol-1-yl)ethylidene]aminox-
ybutanoic acid;

5-[1-(3-n-butyloxyphenyl)-2-(imidazol-1-yl)e-
thylidene]aminoxypentanoic acid;

ethyl 5-[1-(3-n-butyloxyphenyl)-2-(imidazol-1-yl)e-
thylidene]aminoxypentanoate;

6-[1-cyclohexyl-2-(imidazol-1-yl)ethylidene]aminox-
yhexanoic acid;

3-oxa-6-[1-cyclohexyl-2-(imidazol-1-yl)e-
thylidene]aminoxyhexanoic acid;

5-[1-cycloheptyl-2-(imidazol-1-yl)ethylidene]aminox-
ypentanoic acid;

6-[1-cycloheptyl-2-(imidazol-1-yl)ethylidene]aminox-
yhexanoic acid;

5-[1-n-heptyl-2-(imidazol-1-yl)ethylidene]aminoxypen-
tanoic acid;

5-[1-phenyl-2-(imidazol-1-yl)-2-benzyle-
thylidene]aminoxypentanoic acid;

5-[1-cyclohexyl-2-(imidazol-1-yl)-2-benzyle-
thylidene]aminoxypentanoic acid;

ethyl 5-[1-phenyl-2-imidazol-1-yl)-2-benzyle-
thylidene]aminoxypentanoate;

ethyl 5-[1-cyclohexyl-2-(imidazol-1-yl)-2-benzyle-
thylidene]aminoxypentanoate;

6-[1-phenyl-2-(imidazol-1-yl)-2-benzyle-
thylidene]aminoxyhexanoic acid;

6-[1-cyclohexyl-2-(imidazol-1-yl)-2-benzyle-
thylidene]aminoxyhexanoic acid;

5-[1-(4-fluorophenyl)-2-(imidazol-1-yl)-2-(4-fluoroben-
zyl)ethylidene]aminoxypentanoic acid;

5-[1-cyclohexyl-2-(imidazol-1-yl)-2-(4-fluorobenzyl)e-
thylidene]aminoxypentanoic acid; and 3-oxa-5-[1-phenyl-2-(imidazol-1-yl)-2-benzyle-
thylidene]aminoxypentanoic acid;

or a pharmaceutically acceptable salt thereof.

5. A pharmaceutical composition containing a suitable carrier and/or diluent and, as an active principle, a therapeutically effective amount of a compound of formula (I) as defined in claim 1, or a pharmaceutically acceptable salt thereof.

6. A method of treating a disease related to an enhancement of thromboxane $A_2$ synthesis, comprising administering to a human or animal patient in need thereof a therapeutically effective amount of a compound of formula (I) or salt thereof, as defined in claim 1.

7. A method of treating nephropathies, comprising administering to a human or animal patient in need thereof a therapeutically effective amount of a compound of formula (I) or a salt thereof, as defined in claim 1.

8. A method of preventing and/or treating cyclosporine A-induced nephrosis, comprising administering to a human or animal patient in need thereof a therapeutically effective amount of a compound of formula (I) or a salt thereof as defined in claim 1.

9. A method of treating hyperlipidaemia secondary to nephrotic syndrome, comprising administering to a human or animal patient in need thereof a therapeutically effective amount of a compound of formula (I) or a salt thereof, as defined in claim 1.

* * * * *

UNITED STATES PATENT AND TRADEMARK OFFICE
CERTIFICATE OF CORRECTION

PATENT NO. : 5,280,033

DATED : January 18, 1994

INVENTOR(S) : Paolo COZZI et al

It is certified that error appears in the above-identified patent and that said Letters Patent is hereby corrected as shown below:

On title page, item [54] and col. 1, line 6, change
"SYNTHEIS" to -- SYNTHESIS --.

On the title page, item [75], first line, change "Marla" to -- Maria --.

Signed and Sealed this

Eighth Day of November, 1994

Attest:

BRUCE LEHMAN

Attesting Officer

Commissioner of Patents and Trademarks